US007087082B2

(12) United States Patent
Paul et al.

(10) Patent No.: US 7,087,082 B2
(45) Date of Patent: Aug. 8, 2006

(54) BONE IMPLANTS WITH CENTRAL CHAMBERS

(75) Inventors: David C. Paul, Phoenixville, PA (US); Hansjuerg W. Emch, Philadelphia, PA (US); Beat Schenk, Nuglar (CH); Michael L. Boyer, II, Paoli, PA (US); Thomas B. Higgins, Berwyn, PA (US)

(73) Assignee: Synthes (USA), West Chester, PA (US)

( * ) Notice: Subject to any disclaimer, the term of this patent is extended or adjusted under 35 U.S.C. 154(b) by 745 days.

(21) Appl. No.: 09/814,214

(22) Filed: Mar. 22, 2001

(65) Prior Publication Data

US 2002/0029084 A1    Mar. 7, 2002

Related U.S. Application Data

(63) Continuation-in-part of application No. 09/363,844, filed on Jul. 30, 1999, now Pat. No. 6,258,125.

(60) Provisional application No. 60/191,099, filed on Mar. 22, 2000, provisional application No. 60/095,209, filed on Aug. 3, 1998.

(51) Int. Cl.
*A61F 2/44* (2006.01)
(52) U.S. Cl. .................... 623/17.11; 623/16.11; 623/23.63; 623/925
(58) Field of Classification Search ............ 623/23.51, 623/23.61, 23.63, 16.11, 925; 606/60–75
See application file for complete search history.

(56) References Cited

U.S. PATENT DOCUMENTS

| 4,501,269 A | 2/1985 | Bagby ................ 128/92 G |
| 4,858,603 A | 8/1989 | Clemow et al. ...... 128/92 ZW |
| 4,863,472 A | 9/1989 | Törmälä et al. ............ 623/16 |
| 4,936,848 A | 6/1990 | Bagby ........................ 623/17 |
| 4,950,296 A | 8/1990 | McIntyre .................... 623/16 |
| 4,961,740 A | 10/1990 | Ray et al. ................... 606/61 |
| 5,026,373 A | 6/1991 | Ray et al. ................... 606/61 |
| 5,084,051 A | 1/1992 | Törmälä et al. ............ 606/77 |
| 5,112,354 A | 5/1992 | Sires ........................... 623/16 |
| 5,141,510 A | 8/1992 | Takagi et al. ............... 623/16 |
| 5,192,327 A | 3/1993 | Brantigan ................... 623/17 |
| 5,425,772 A | 6/1995 | Brantigan ................... 623/17 |
| 5,492,697 A | 2/1996 | Boyan et al. ............. 424/422 |
| 5,514,180 A | 5/1996 | Heggeness et al. ......... 623/17 |
| 5,522,899 A | 6/1996 | Michelson .................. 623/17 |
| 5,549,679 A | 8/1996 | Kuslich ....................... 623/17 |
| 5,571,192 A | 11/1996 | Schönhöffer ............... 623/17 |

(Continued)

FOREIGN PATENT DOCUMENTS

DE         42 42 889 A1     6/1994

(Continued)

OTHER PUBLICATIONS

Bill Hylton, *Rodale's Illustrated Cabinetmaking*, Rodale Press, Inc., Emmaus, Pennsylvania, 1998.

(Continued)

*Primary Examiner*—David J. Isabella
*Assistant Examiner*—Urmi Chattopadhyay
(74) *Attorney, Agent, or Firm*—Jones Day

(57) ABSTRACT

A bone fusion implant for repair or replacement of bone includes a hollow body formed from at least two bone fragments which are configured and dimensioned for mutual engagement and which are coupled together. The hollow body may be formed of autograft, allograft, or xenograft bone tissue, and may include a core formed of at least one of bone material and bone inducing substances, with the core being disposed in the hollow body.

17 Claims, 27 Drawing Sheets

U.S. PATENT DOCUMENTS

| | | | | |
|---|---|---|---|---|
| 5,591,235 | A | 1/1997 | Kuslich | 623/17 |
| 5,593,409 | A | 1/1997 | Michelson | 606/61 |
| 5,609,635 | A | 3/1997 | Michelson | 623/17 |
| 5,645,598 | A | 7/1997 | Brosnahan, III | 623/17 |
| 5,683,394 | A | 11/1997 | Rinner | 606/86 |
| 5,702,449 | A | 12/1997 | McKay | 623/17 |
| 5,702,453 | A | 12/1997 | Rabbe et al. | 623/17 |
| 5,702,455 | A | 12/1997 | Saggar | 623/17 |
| 5,709,683 | A | 1/1998 | Bagby | 606/61 |
| 5,716,415 | A | 2/1998 | Steffee | 623/17 |
| 5,728,159 | A | 3/1998 | Stroever et al. | 623/16 |
| 5,741,253 | A | 4/1998 | Michelson | 606/61 |
| 5,766,252 | A | 6/1998 | Henry et al. | 623/17 |
| 5,766,253 | A | 6/1998 | Brosnahan, III | 623/17 |
| 5,769,897 | A | 6/1998 | Härle | 623/16 |
| 5,776,197 | A | 7/1998 | Rabbe et al. | 623/17 |
| 5,776,198 | A | 7/1998 | Rabbe et al. | 623/17 |
| 5,776,199 | A | 7/1998 | Michelson | 623/17 |
| 5,782,830 | A | 7/1998 | Farris | 606/61 |
| 5,785,710 | A | 7/1998 | Michelson | 606/61 |
| 5,814,084 | A | 9/1998 | Grivas et al. | 623/16 |
| 5,885,299 | A | 3/1999 | Winslow et al. | 606/99 |
| 5,888,222 | A | 3/1999 | Coates et al. | 623/17 |
| 5,895,426 | A * | 4/1999 | Scarborough et al. | 623/17.16 |
| 5,899,939 | A | 5/1999 | Boyce et al. | 623/16 |
| 5,910,315 | A | 6/1999 | Stevenson et al. | 424/422 |
| 5,968,098 | A | 10/1999 | Winslow | 623/17 |
| 5,972,368 | A | 10/1999 | McKay | 424/423 |
| 5,980,522 | A | 11/1999 | Koros et al. | 606/61 |
| 5,984,967 | A | 11/1999 | Zdeblick et al. | 623/17 |
| 5,989,289 | A * | 11/1999 | Coates et al. | 623/17.16 |
| 6,005,161 | A | 12/1999 | Brekke et al. | 623/16 |
| 6,008,431 | A | 12/1999 | Caldarise et al. | 623/16 |
| 6,008,433 | A | 12/1999 | Stone | 623/16 |
| 6,025,538 | A | 2/2000 | Yaccarino, III | 623/16 |
| 6,033,405 | A | 3/2000 | Winslow et al. | 606/61 |
| 6,033,438 | A | 3/2000 | Bianchi et al. | 623/17 |
| 6,039,762 | A * | 3/2000 | McKay | 606/60 |
| 6,045,579 | A | 4/2000 | Hochshuler et al. | 623/17 |
| 6,045,580 | A | 4/2000 | Scarborough et al. | 623/17 |
| 6,060,640 | A | 5/2000 | Pauley et al. | 623/11 |
| 6,080,193 | A | 6/2000 | Hochshuler et al. | 623/17 |
| 6,090,998 | A | 7/2000 | Grooms et al. | 623/16 |
| 6,096,081 | A | 8/2000 | Grivas et al. | 623/17.11 |
| 6,111,164 | A | 8/2000 | Rainey et al. | 623/16 |
| 6,123,731 | A * | 9/2000 | Boyce et al. | 523/113 |
| 6,129,763 | A | 10/2000 | Chauvin et al. | 623/17 |
| 6,143,033 | A | 11/2000 | Paul et al. | 623/17.11 |
| 6,156,070 | A | 12/2000 | Incavo et al. | 623/23.52 |
| 6,187,329 | B1 | 2/2001 | Agrawal et al. | 424/426 |
| 6,200,347 | B1 * | 3/2001 | Anderson et al. | 623/11.11 |
| 6,206,923 | B1 | 3/2001 | Boyd et al. | 623/17.11 |
| 6,241,769 | B1 | 6/2001 | Nicholson et al. | 623/17.11 |
| 6,245,108 | B1 | 6/2001 | Biscup | 623/17.11 |
| 6,258,125 | B1 | 7/2001 | Paul et al. | 623/17.11 |
| 6,261,586 | B1 | 7/2001 | McKay | 424/423 |
| 6,264,695 | B1 | 7/2001 | Stoy | 623/17.16 |
| 6,270,528 | B1 | 8/2001 | McKay | 623/17.11 |
| 6,277,149 | B1 | 8/2001 | Boyle et al. | 623/17.16 |
| 2001/0010021 | A1 | 7/2001 | Boyd et al. | 623/17.13 |
| 2001/0016775 | A1 | 8/2001 | Scarborough et al. | 623/17.16 |
| 2001/0016777 | A1 | 8/2001 | Biscup | 623/17.16 |
| 2002/0138143 | A1 * | 9/2002 | Grooms et al. | 623/17.11 |

FOREIGN PATENT DOCUMENTS

| | | |
|---|---|---|
| DE | 44 23 257 A1 | 1/1996 |
| DE | 299 13 200 U1 | 10/1999 |
| FR | 2 753 368 | 3/1998 |
| WO | WO 94/26211 | 11/1994 |
| WO | WO 95/08964 | 4/1995 |
| WO | WO 96/39988 | 12/1996 |
| WO | WO 97/14378 | 4/1997 |
| WO | WO 97/20526 | 6/1997 |
| WO | WO 97/25945 | 7/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09914 | 3/1999 |
| WO | WO 99/38461 | 8/1999 |
| WO | WO 99/56675 | 11/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/40179 | 7/2000 |
| WO | WO 00/41654 | 7/2000 |
| WO | WO 00/42954 | 7/2000 |
| WO | WO 00/59412 | 10/2000 |
| WO | WO 00/74607 | 12/2000 |
| WO | WO 00/74608 | 12/2000 |
| WO | WO 01/08611 A1 | 2/2001 |

OTHER PUBLICATIONS

Wolfram Graubner, *Encyclopedia of Wood Joints*, The Taunton Press, Inc., Newtown, Connecticut, 1992.

Marshall R. Urist, "Surface-Dacalcified Allogeneic Bone (SDAB) Implants. A Preliminary Report of 10 Cases and 25 Comparable Operations With Undecalcified Lyophilized Bone Implants.," *Clinical Orthopaedics and Related Research*, No. 56, pp. 37-50, 1968.

Fred H. Albee, *Bone Graft Surgery in Disease, Injury and Deformity*, D. Appleton-Century Company, Inc., New York, 1940, pp. 30, 114, 151, 155, 164, 212, 256-257, 311-313.

Fred H. Albee, "Bone Surgery With Machine Tools," *Scientific American*, Apr. 1936, pp. 178-181.

Fred H. Albee, *Bone-Graft Surgery*, W. B. Saunders Company, Philadelphia, Pennsylvania, 1915, pp. 145, 165-166, 171, 368-369.

* cited by examiner

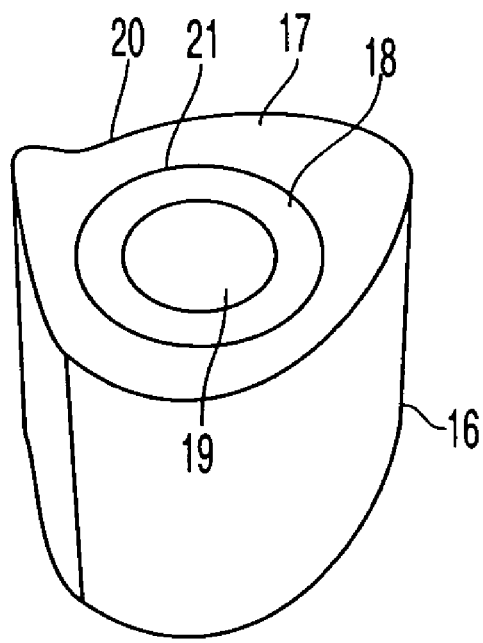
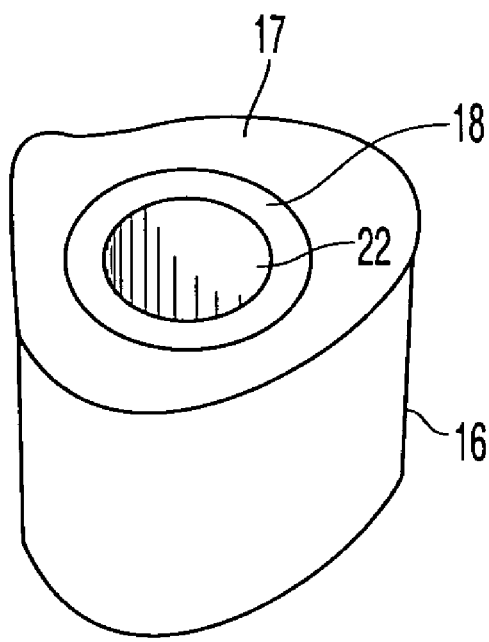
FIG. 1G FIG. 1H
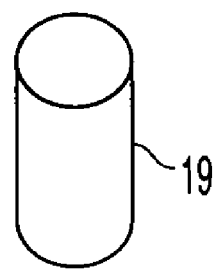
FIG. 1I

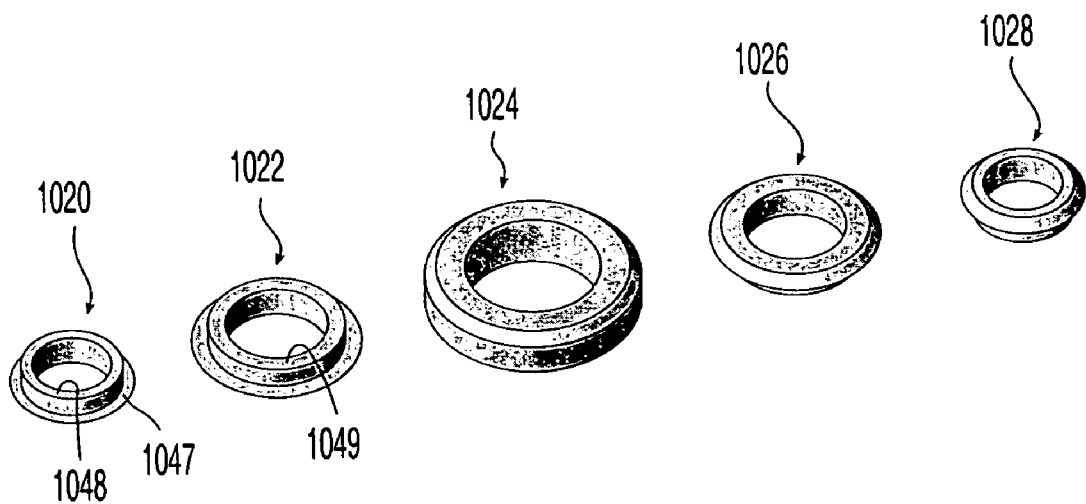
FIG. 7A
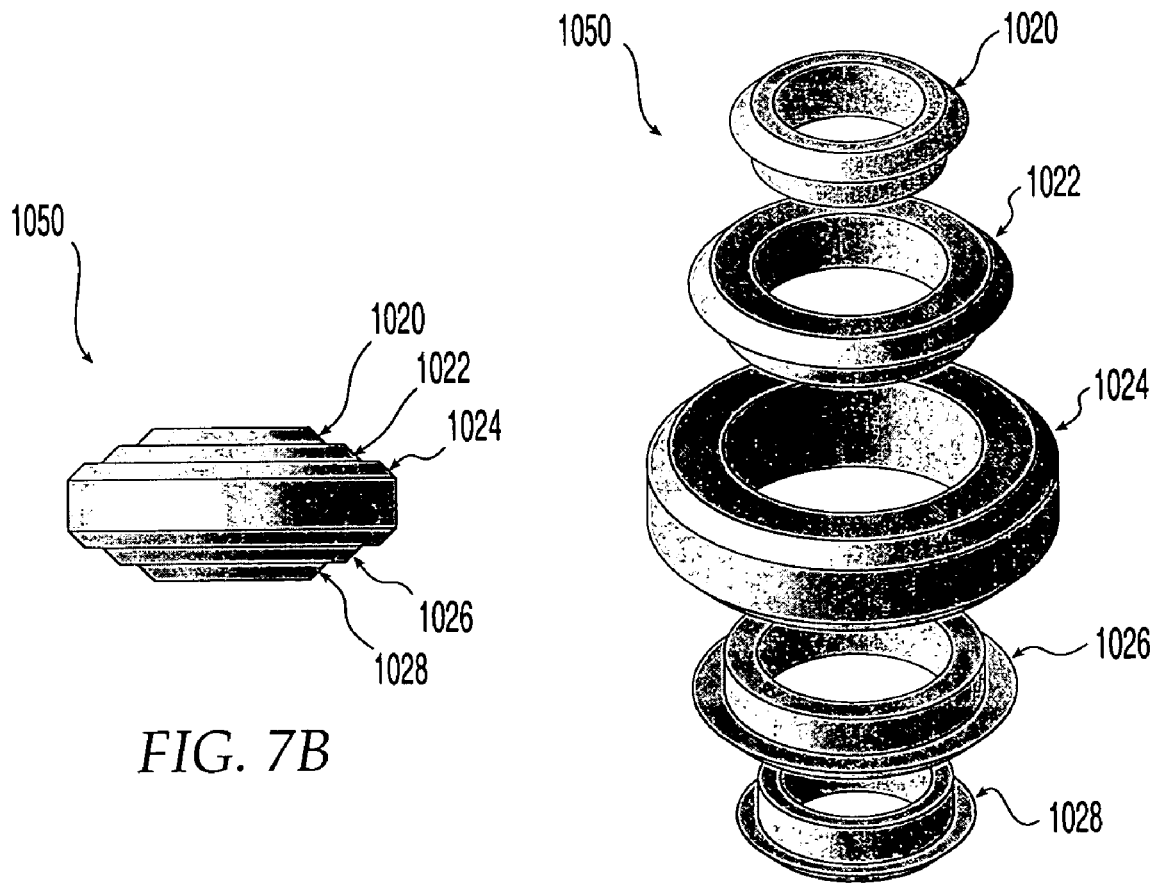
FIG. 7B
FIG. 7C

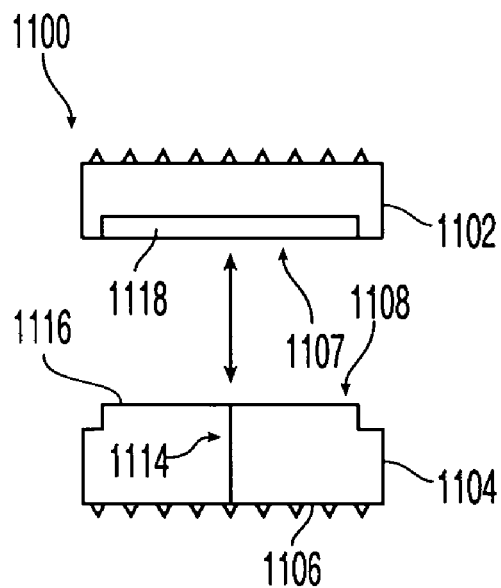
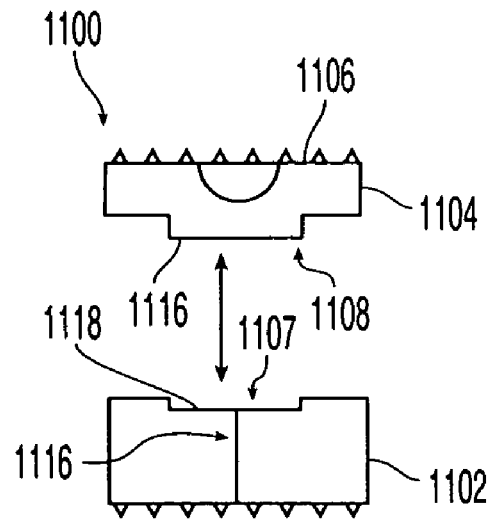
*FIG. 8A*  *FIG. 8B*
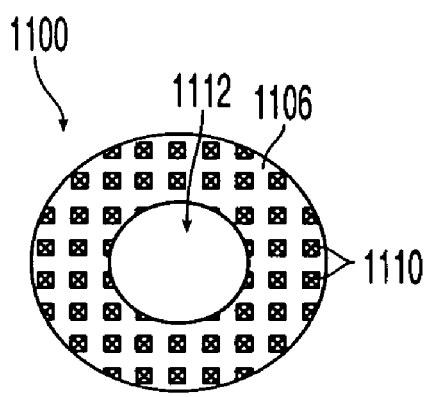
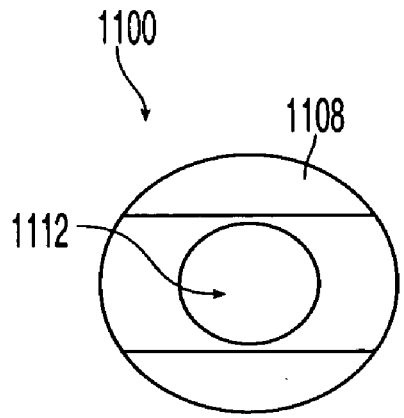
*FIG. 8C*  *FIG. 8D*
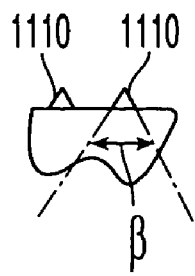
*FIG. 8E*

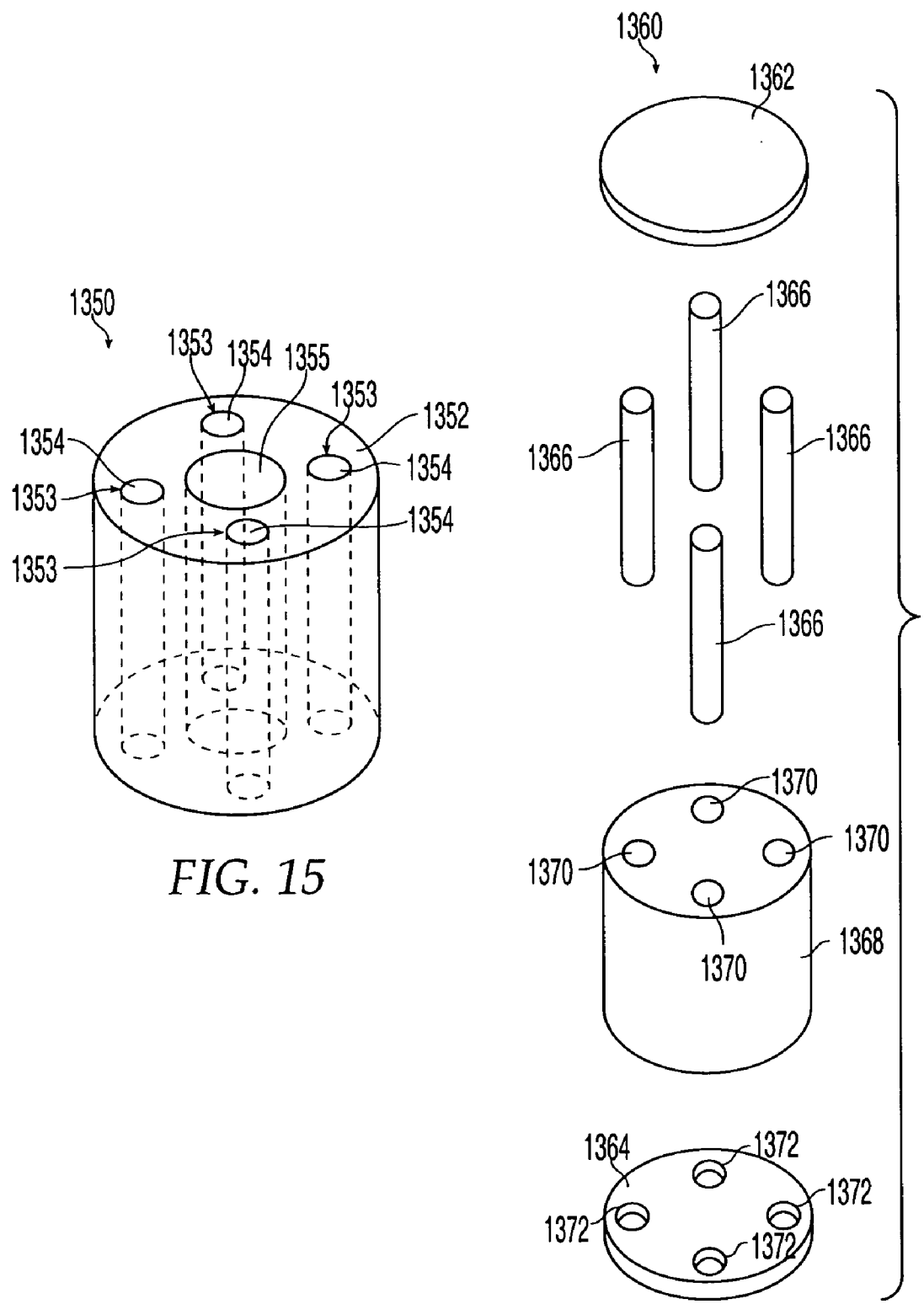

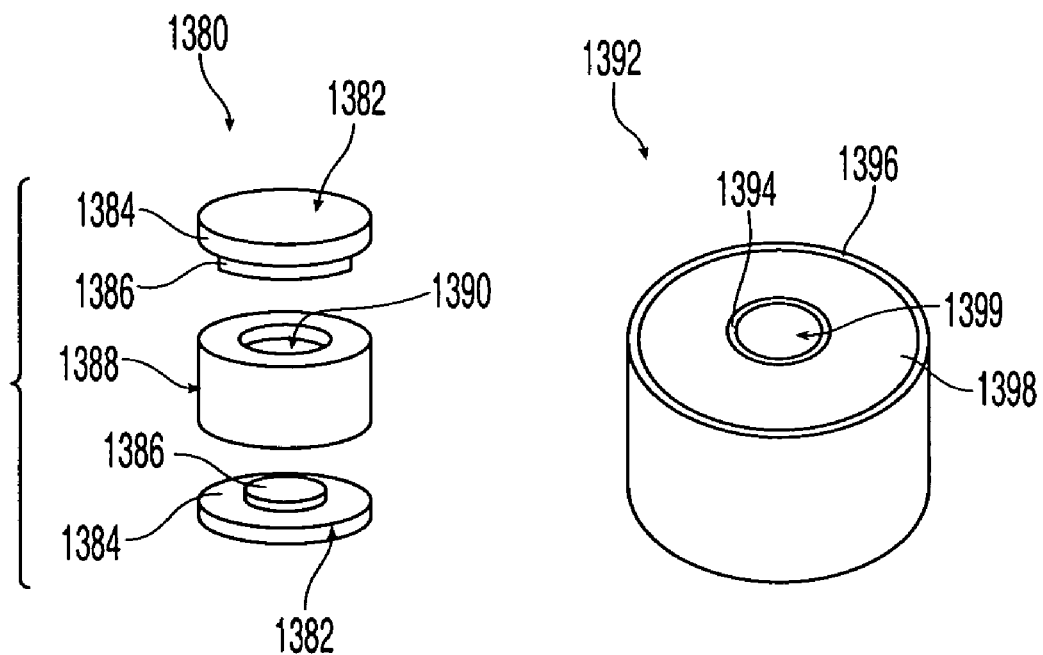
FIG. 17
FIG. 18
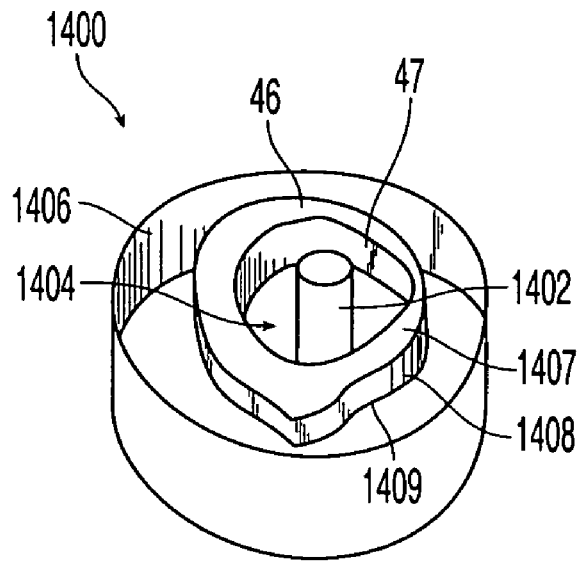
FIG. 19A
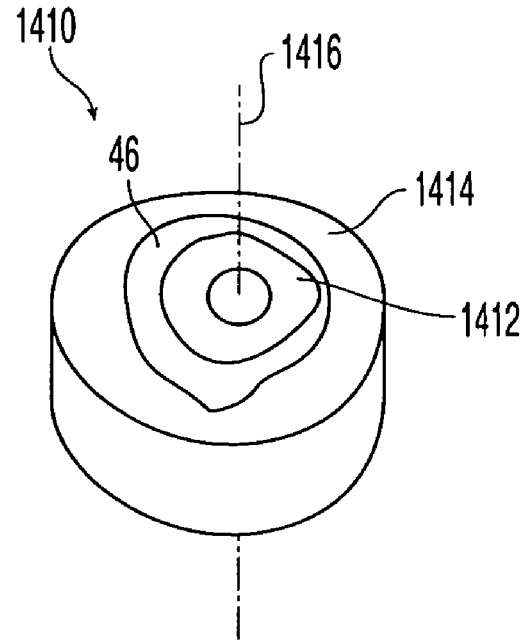
FIG. 19B

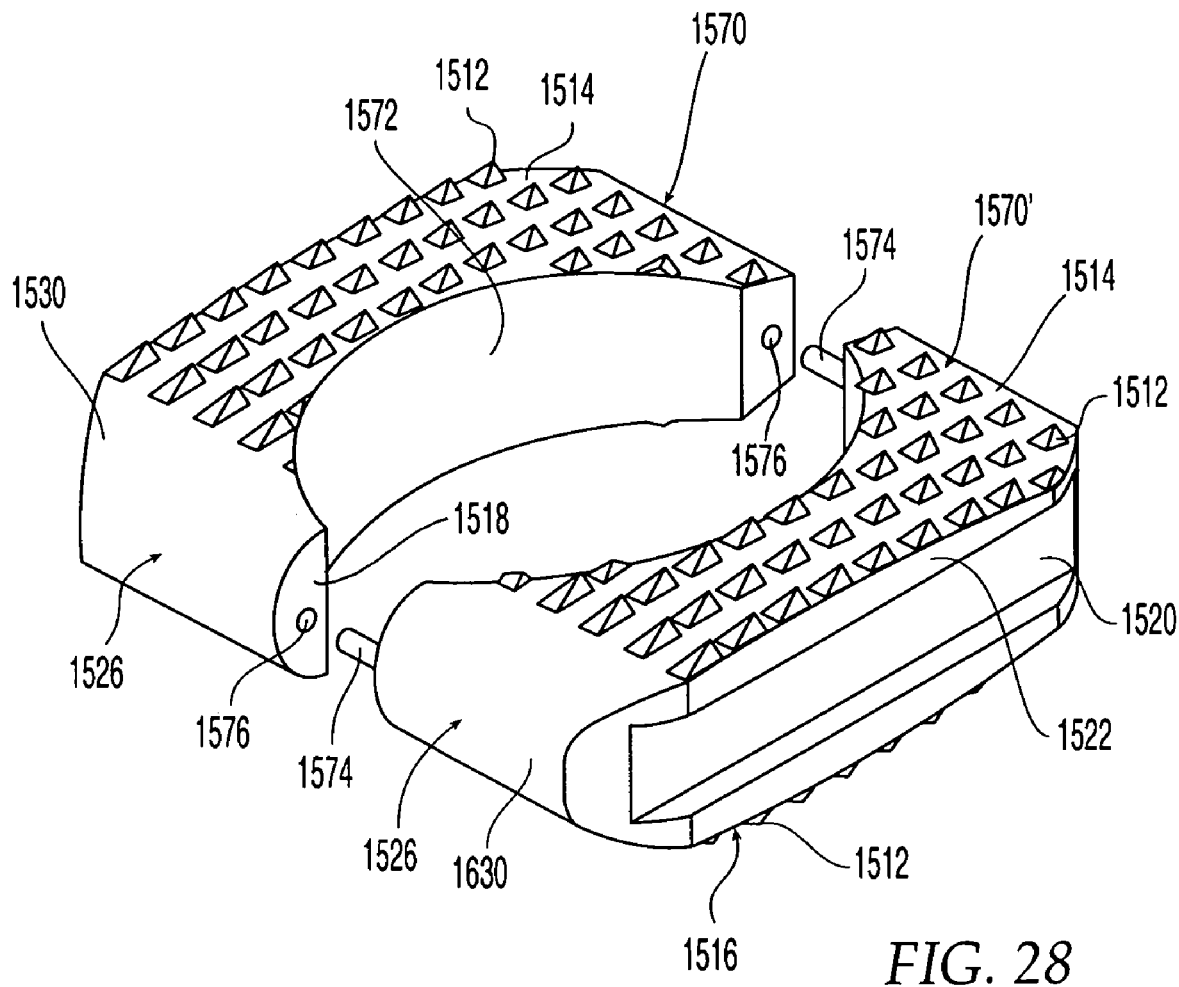
FIG. 28
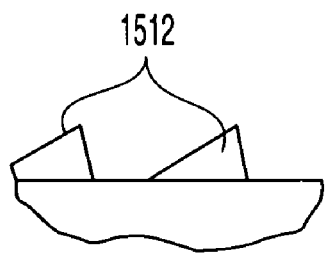   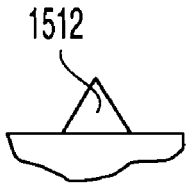
FIG. 29A        FIG. 29B

BONE IMPLANTS WITH CENTRAL CHAMBERS

CROSS-REFERENCE TO RELATED APPLICATIONS

This is a continuation-in-part of U.S. patent application Ser. No. 09/363,844, filed Jul. 30, 1999, now U.S. Pat. No. 6,258,125, which claims the benefit under 35 U.S.C. § 119(e) of Provisional Application No. 60/095,209, filed Aug. 3, 1998; this application further claims the benefit under 35 U.S.C. § 119(e) of Provisional Application No. 60/191,099, filed Mar. 22, 2000.

FIELD OF THE INVENTION

The invention relates to an implant for orthopedic applications. More particularly, the invention is related to an implant formed from two or more bone portions. In addition, the invention relates to allogenic intervertebral implants.

BACKGROUND OF THE INVENTION

Bone grafts have become an important and accepted means for treating bone fractures and defects. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. This is primarily due to the limited applicability of xenografts, transplants from another species.

Orthopedic autografts or autogenous grafts involve source bone acquired from the same individual that will receive the transplantation. Thus, this type of transplant moves bony material from one location in a body to another location in the same body, and has the advantage of producing minimal immunological complications. It is not always possible or even desirable to use an autograft. The acquisition of bone material from the body of a patient typically requires a separate operation from the implantation procedure. Furthermore, the removal of material, oftentimes involving the use of healthy material from the pelvic area or ribs, has the tendency to result in additional patient discomfort during rehabilitation, particularly at the location of the material removal. Grafts formed from synthetic material have also been developed, but the difficulty in mimicking the properties of bone limits the efficacy of these implants.

As a result of the challenges posed by autografts and synthetic grafts, many orthopedic procedures alternatively involve the use of allografts, which are bone grafts from other human sources (normally cadavers). The bone grafts, for example, are placed in a host bone and serve as the substructure for supporting new bone tissue growth from the host bone. The grafts are sculpted to assume a shape that is appropriate for insertion at the fracture or defect area, and often require fixation to that area as by screws or pins. Due to the availability of allograft source material, and the widespread acceptance of this material in the medical community, the use of allograft tissues is certain to expand in the field of musculoskeletal surgery.

FIGS. 1A, 1B, 1C, and 1D show the relative sizes of the femur 10 (thigh), tibia 11 (lower leg), humerus 12 (upper arm), and radius 13 (lower arm) respectively for an adult. As can be seen when comparing these bones, their geometry varies considerably. The lengths of these bones may have a range, for example, from 47 centimeters (femur), to 26 centimeters (radius). In addition, as shown in FIGS. 1E and 1F, the shape of the cross section of each type of bone varies considerably, as does the shape of any given bone over its length. While the femur 10, as shown in FIG. 1E, has a generally rounded outer shape, the tibia 11 has a generally triangular outer shape as shown in FIG. 1F. The wall thickness also varies in different areas of the cross-section of each bone. For example, femur 10 has a wall thickness $X_1$ that is much smaller than wall thickness $X_2$. Similarly, tibia 11 has a wall thickness $X_3$ that is much smaller than wall thickness $X_4$. Even after clearing the inner canal regions 14 and 15 within the bones, the contours of these canals vary considerably. Thus, machining of the bone to have standardized outer dimensions and/or canal dimensions is necessary in many applications.

Sections of bones with regions having narrow cross-sections, as seen for example with thicknesses $X_1$ and $X_3$, may be rejected for use in certain applications because the wall thickness does not have sufficient strength. Preferably, no region of a bone section has a thickness less than 5 millimeters, although in some applications smaller wall thicknesses may be employed. Thus, in the case that a bone section is found to have a region with a wall thickness less than a minimum acceptable thickness, such a bone section is rejected as being unsuitable for use in a bulk configuration. Often, such a section is ground into bone particulate that is then used in other applications. The minimum thickness standards imposed on the use of bone sections results in the rejection of substantial quantities of bone sections, and thus an inefficient use of the material. Bone sections that do not meet the minimum thickness standards are often found in older individuals.

As a collagen-rich and mineralized tissue, bone is composed of about forty percent organic material (mainly collagen), with the remainder being inorganic material (mainly a near-hydroxyapatite composition resembling $3Ca_3(PO_4)_2.Ca(OH)_2$). Structurally, the collagen assumes a fibril formation, with hydroxyapatite crystals disposed along the length of the fibril, and the individual fibrils are disposed parallel to each other forming fibers. Depending on the type of bone, the fibrils are either interwoven, or arranged in lamellae that are disposed perpendicular to each other.

There is little doubt that bone tissues have a complex design, and there are substantial variations in the properties of bone tissues with respect to the type of bone (i.e., leg, arm, vertebra) as well as the overall structure of each type. For example, when tested in the longitudinal direction, leg and arm bones have a modulus of elasticity of about 17 to 19 GPa, while vertebra tissue has a modulus of elasticity of less than 1 GPa. The tensile strength of leg and arm bones varies between about 120 MPa and about 150 MPa, while vertebra have a tensile strength of less than 4 MPa. Notably, the compressive strength of bone varies, with the femur and humerus each having a maximum compressive strength of about 167 MPa and 132 MPa respectively. Again, the vertebra have a far lower compressive strength of no more than about 10 MPa.

With respect to the overall structure of a given bone, the mechanical properties vary throughout the bone. For example, a long bone (leg bone) such as the femur has both compact bone and spongy bone. Cortical bone, the compact and dense bone that surrounds the marrow cavity, is generally solid and thus carries the majority of the load in major bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10–20 MPa and a density of about 0.7, cortical bone has a tensile strength of about 100–200 MPa and a density of about 2. Additionally, the strain to failure of cancellous bone is about 5–7%, while cortical bone can only withstand 1–3% strain before failure. It should also be noted that these mechanical characteristics may degrade as a result of numerous factors such as any chemical treatment applied to the bone material, and the manner of storage after removal but prior to implantation (i.e. drying of the bone).

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. Thus, the design of an implant using cancellous bone may be tailored to specifically incorporate material of a desired porosity.

It is essential to recognize the distinctions in the types and properties of bones when considering the design of implants. Surgeons often work with bones using similar tools as would be found in carpentry, adapted for use in the operating room environment. This suggests that bones have some properties which are similar to some types of wood, for example ease in sawing and drilling. Notably, however, are many differences from wood such as the abrasive nature of hydroxyapatite and the poor response to local heating during machining of a bone. The combination of tensile and compressive strengths found in bone, resulting from the properties of the collagen and hydroxyapatite, is thus more aptly compared to the tensile and compressive strengths found in reinforced concrete, due to steel and cement. Furthermore, while wood is readily available in considerable quantity, bone material is an extremely limited resource that must be used in an extremely efficient manner.

Various types of bone grafts are known. For example, as disclosed in U.S. Pat. No. 5,989,289 to Coates et al., a spinal spacer includes a body formed of a bone composition such as cortical bone. The spacer has walls that define a chamber that is sized to receive an osteogenic composition to facilitate bone growth.

U.S. Pat. No. 5,899,939 to Boyce et al. discloses a bone-derived implant for load-supporting applications. The implant has one or more layers of fully mineralized or partially demineralized cortical bone and, optionally, one or more layers of some other material. The layers constituting the implant are assembled into a unitary structure, as by joining layers to each other in edge-to-edge fashion in a manner analogous to planking.

Another bone-grafting material is disclosed in U.S. Pat. No. 4,678,470 to Nashef et al., and is formed using a tanning procedure involving glutaraldehyde that renders the material osteoinvasive. A bone block is shaped into a precise predetermined form and size using conventional machining techniques. A paste-like suspension is also formed using known methods of comminuting bone, such as milling, grinding, and pulverizing, and adding the pulverized or powdered bone to a carrier. The treatment with glutaraldehyde allows the use of bovine, ovine, equine, and porcine bone sources. However, if the final desired form of the bone grafting material is a block of bone or machined shape, the bone stock must be large enough to provide a block of the required size.

U.S. Pat. No. 5,981,828 to Nelson et al. discloses a "composite" acetabular allograft cup for use in hip replacement surgery. A press is used to form the cup from impacted cancellous bone chips and cement. The composite is a hollow hemispherical dome having an outer surface comprised essentially of exposed cancellous bone chips and an inner surface comprised essentially of hardened bone cement. The cancellous bone chips are first placed in a mold and subjected to a load to form a compact and consolidated mass that conforms to the shape of the mold. The mold is then opened, cement is applied, and the mold is then reapplied. While an allograft of a particular shape may be formed using this process, the process is limited to forming an allograft by compressing cancellous bone chips. Thus, numerous molds are required in order to produce allografts of different sizes, and the use of bulk-size allograft source material is not facilitated.

With a rapidly increasing demand in the medical profession for devices incorporating bone material, the tremendous need for the tissue material itself, particularly allograft tissue material, presents a considerable challenge to the industry that supplies the material. Due to the size and shape of the bones from which the material is harvested, and the dimensional limitations of any particular type of bone in terms of naturally occurring length and thickness (i.e. cortical or cancellous), there is a need for a means by which individual bone fragments can be combined to form larger, integral implants that are more suitable for use in areas of larger fractures or defects. For example, the size of cortical bone fragments needed to repair a fracture or defect site is often not available in a thick enough form. While multiple fragments may together meet the size and shape requirements, several prominent concerns have placed a practical limitation on the implementation of this concept. There is considerable uncertainty regarding the structural integrity provided by fragments positioned adjacent to one another without bonding or other means of securing the fragments to each other. Moreover, there is concern over the possibility that a fragment may slip out of position, resulting in migration of the fragment and possible further damage in or near the area of implantation.

In addition, due to the geometry of bones such as the femur and tibia, all portions of the bones are not readily usable as a result of size limitations. Thus, prior art implants, specifically allografts, are produced with an inefficient use of source bones.

Turning to exemplar uses for implants formed from bone, a number of medical conditions such as compression of spinal cord nerve roots, degenerative disc disease, and spondylolisthesis can cause severe low back pain. Intervertebral fusion is a surgical method of alleviating low back pain. In posterior lumbar interbody fusion ("PLIF"), two adjacent vertebral bodies are fused together by removing the affected disc and inserting an implant that would allow for bone to grow between the two vertebral bodies to bridge the gap left by the disc removal.

A number of different implants and implant materials have been used in PLIF with varying success. Current implants used for PLIF include threaded titanium cages and allografts. Threaded titanium cages suffer from the disadvantage of requiring drilling and tapping of the vertebral end plates for insertion. In addition, the incidence of subsidence in long term use is not known. Due to MRI incompatibility of titanium, determining fusion is problematic. Finally, restoration of lordosis, i.e., the natural curvature of the lumbar spine is very difficult when a cylindrical titanium cage is used.

As discussed above, allografts are sections of bone that may be taken from a long bone of a donor. A cross section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They are also MRI compatible so that fusion can be more accurately ascertained and promote the formation of bone, i.e., osteoconductive. Although the osteoconductive nature of the allograft provides a biological interlocking between the allograft and the vertebrae for long term mechanical strength, initial and short term mechanical strength of the interface between the allograft and the vertebrae are lacking as evidenced by the possibility of the allograft being expelled after implantation.

Currently commercially available allografts are simply sections of bone not specifically designed for use in PLIF. As a result, the fusion of the vertebral bodies does not occur in optimal anatomical position. A surgeon may do some minimal intraoperative shaping and sizing to customize the allograft for the patient's spinal anatomy. However, significant shaping and sizing of the allograft is not possible due to the nature of the allograft. Even if extensive shaping and sizing were possible, a surgeon's ability to manually shape and size the allograft to the desired dimensions is severely limited.

Most PLIF implants, whether threaded cages or allograft, are available in different sizes and have widths that vary with the implant height. For example, the width of a cylindrical cages will be substantially equivalent to the height. Although larger heights may be clinically indicated, wider implants are generally not desirable since increased width requires removal of more of the facet, which can lead to decreases stability, and more retraction of nerve roots, which can lead to temporary or permanent nerve damage.

There is a need for new, fundamental approaches to working with and processing tissues, in particular allograft material, especially with regard to machining, mating, and assembling bone fragments. Specifically, there is a need for an implant that allows more efficient use of source material. More specifically, there is a need for an implant that is an integrated implant comprising two or more bone fragments that are interlocked to form a mechanically effective, strong unit. There also is a need for an improved implant for fusing vertebrae.

SUMMARY OF THE INVENTION

The present invention is related to an implant including a body having an inner sheath and at least one outer sheath. Each sheath is formed from a different bone and has an interior surface and an exterior surface. The exterior surface of each outer sheath contacts the interior surface of no more than one other outer sheath. In one embodiment, a core is disposed in the inner sheath and is formed from a bone other than the bones of the sheaths. The core can be formed of cancellous bone, while at least one sheath can be formed of cortical bone. In another embodiment, at least one sheath can be formed of cancellous bone and the core can be formed of cortical bone. The bones are at least one of autograft, allograft, and xenograft bone tissue, and the bone tissue of at least one bone may be partially demineralized or demineralized. In a further embodiment, the body is formed from a cross-section of the sheaths and core, with the cross-section including at least a portion of each sheath and core. The sheaths and core can be coupled together with at least one fastener that may intersect each of the sheaths and core, with the fastener being a screw, key, pin, peg, rivet, cotter, nail, spike, bolt, stud, staple, boss, clamp, clip, dowel, stake, hook, anchor, tie, band, crimp, or wedge. Also, the sheaths and core can be bonded together with a bonding agent. At least one sheath may be packed with bone growth materials and may include alignment indicia. The exterior surface may be separated from a portion of the interior surface.

At least one of the inner sheath, an outer sheath, and the core can be at least partially dehydrated to fit against a surrounding mating surface. Furthermore, at least one of the inner sheath, an outer sheath, and the core can be at least partially dehydrated to fit within a surrounding inner sheath or outer sheath provided with a greater moisture content.

Contacting surfaces of adjacent sheaths can be machined surfaces so that the contour of the contacting surfaces is about the same. The machined surfaces permit press-fitting of one sheath into another sheath. In some embodiments, the bones are selected from a femur, tibia, humerus, fibula, ulna, and radius.

At least one supplemental sheath having an interior surface and an exterior surface also may be included, with the exterior surface of each supplemental sheath contacting the interior surface of no more than one other sheath and the interior surface of each supplemental sheath contacting the exterior surface of no more than one other sheath. The at least one supplemental sheath is formed of a material selected from metals, alloys, ceramics, polymers, and composites.

The present invention is also related to an implant having a body formed from a cross-section of a core and a plurality of sheaths. Each sheath has an inner surface and an outer surface, and at least two sheaths are formed from different bones. The outer surface of a first sheath has about the same contour as the inner surface of a second sheath so that the first and second sheaths mate together, and the cross-section includes at least a portion of each sheath and core. The core may be formed from a bone other than the bones of the sheaths, and in one embodiment the core is formed of cancellous bone and at least one sheath is formed of cortical bone. In another embodiment, at least one sheath is formed of cancellous bone and the core is formed of cortical bone.

Also, the present invention is related to an implant with a body that includes at least one sheath defining a hole, with a core fit therein. The body is formed from at least two different bones selected from a femur, tibia, humerus, fibula, ulna, and radius.

Furthermore, the present invention is related to an implant with a body having two outer annular members and at least one inner annular member. At least one of the annular members is formed from bone and the annular members are coupled together to create a central chamber. In one embodiment, each annular member has at least one surface that is press-fit with the surface of another annular member. The outside diameter of the outer annular members may be smaller than the outside diameter of the at least one inner annular member. The implant can be symmetrical about an innermost annular member, with the diameter of the implant progressively decreasing from the innermost annular member to each outer annular member. The central chamber can be packed with at least one of bone material and bone inducing substances.

In one embodiment, at least one annular member is formed of cancellous bone and at least one annular member is formed of cortical bone. A plurality of annular members may be coupled together with at least one fastener. Also, a plurality of annular members may be bonded together with a bonding agent. In some embodiments, the annular members have non-circular shapes, such as generally oblong shapes. At least one supplemental annular member may be coupled to at least one of the annular members formed from bone, with the at least one supplemental annular member being formed of a material selected from metals, alloys, ceramics, polymers, and composites. At least one annular member may include alignment indicia, and adjacent surfaces of at least two annular members may not completely contact each other.

The invention further relates to an implant with a body having at least two ring-shaped members formed from bone that are coupled together to create a central chamber. The ring-shaped members may have ridges that mate and press-fit together.

Another implant of the present invention includes at least two layers of bone components coupled to each other, the components together defining at least one securing region, and at least one insertable securing element adapted for placement in the at least one securing region. The at least one securing region may be a recess or hole, and each layer may be formed from a different bone selected from a femur, tibia, humerus, fibula, ulna, and radius. At least one layer may be formed of cancellous bone and at least one layer may be formed of cortical bone. Also, the layers may include at least one of autograft, allograft, and xenograft bone tissue, and the layers may be bonded together with a bonding agent. The bone tissue of at least one bone may be partially demineralized or demineralized, and the layers may be bonded together with a bonding agent. A first layer may be at least partially dehydrated to mate against at least one other layer. Adjacent layers may be provided with mutually contacting surfaces that are machined to have about the same contour, and the contacting surfaces of adjacent layers may be press-fit together.

In addition, the implant may further include at least one supplemental layer coupled to at least one of the layers of bone components, with the at least one supplemental layer being formed of a material selected from metals, alloys, ceramics, polymers, and composites. Also, the implant may further include a chamber packed with bone growth materials. In some embodiments, at least one layer includes alignment indicia, and the outer surface may be separated from a portion of the inner surface.

The present invention is further related to a hollow body having a minimum wall thickness, the body being formed from a plurality of portions of bone sections with each section having a thick-walled portion and a thin-walled portion. The thick-walled portion has a wall thickness at least as thick as the minimum wall thickness, and the thin-walled section has a wall thickness less than the minimum wall thickness. Only thick-walled portions are coupled together to form the body. The thick-walled portions are coupled together with at least one portion having a first coupling and at least one portion having a second coupling, with the portions being joined together by interfitting together the first and second couplings. At least one coupling may be at least partially dehydrated to mate against another coupling. In one embodiment, the first coupling is a male coupling and the second coupling is a female coupling so that the portions are mated in a male-female relationship. The male coupling may be a tenon and the female coupling may be a mortise, or the male coupling may be a tongue and the female coupling may be a groove.

The present invention is also related to an implant including a layer formed of a first bone and at least one layer formed by a curable carrier, with the at least one layer being molded to the first bone. The layer formed of a first bone may include a primary sleeve with a top surface, a bottom surface, an inner surface, and an outer surface, with the at least one layer of curable carrier being molded to the inner surface or the outer surface. In one embodiment, the curable carrier further includes bone or ceramic in powder, chips, or fibers. At least one secondary sleeve may be provided, with each secondary sleeve being coupled to a primary sleeve or another secondary sleeve by a layer of curable carrier.

Additionally, the present invention is related to a method of forming an implant including: surrounding at least a portion of a bone section with a first mold to create a cavity therebetween; filling the cavity with a first substance, and coupling the first substance to the bone section. The first substance may be at least one of a curable carrier, bone powder, bone chips bone fibers, or ceramic, and be coupled to the bone section by curing or by compaction.

Furthermore, the present invention is related to a bone fusion implant for repair or replacement of bone that includes a hollow body formed from at least two bone fragments which are configured and dimensioned for mutual engagement and which are coupled together. In some embodiments, at least one bone fragment has a first coupling portion and at least one bone fragment has a second coupling portion, with the bone fragments being joined together by intermitting together the first and second coupling portions. The first coupling portion may be a male coupling portion and the second coupling portion may be a female coupling portion so that the bone fragments are mated in a male-female relationship. The male coupling portion may be a tenon and the female coupling portion may be a mortise, or the male coupling portion may be a tongue and the female coupling portion may be a groove. The fragments may be configured and dimensioned to form a dovetail joint. At least two bone fragments may be concentric hollow cylinders. The implant may additionally include a core formed of at least one of bone material and bone inducing substances, with the core being disposed in the hollow body. The core may be formed of cancellous bone with a fluid concentrated therein, and the cancellous bone may be subjected to mechanical pressure to concentrate the fluid such as by using mechanical pressure that is applied by aspiration. The fluid also may be concentrated by soaking.

The hollow body may be formed using at least one of autograft, allograft, and xenograft bone tissue, and at least one bone fragment may be partially demineralized or demineralized. At least one of the bone fragments may be at least partially dehydrated to mate against another bone fragment. In addition, the hollow body may form a completely enclosed hollow region.

An allogenic intervertebral implant for fusing vertebrae also is disclosed. The implant is a piece of allogenic bone conforming in size and shape with a portion of an end plate of a vertebra. The implant has a wedge-shaped profile to restore disc height and the natural curvature of the spine. The top and bottom surfaces of the implant have a plurality of teeth to resist expulsion and provide initial stability. The implant according to the present invention provides initial stability need for fusion without stress shielding.

Thus, the present invention further relates to an allogenic intervertebral implant for use when surgical fusion of vertebral bodies is indicated. The implant comprises a piece of allogenic bone conforming in size and shape with a portion of an end plates of the vertebrae and has a wedge-shaped profile with a plurality of teeth located on top and bottom surfaces. The top and bottom surfaces can be flat planar surfaces or curved surfaces to mimic the topography of the end plates. The implant has a channel on at least one side for receiving a surgical tool. This channel runs in the anterior direction to accommodate a variety of surgical approaches. A threaded hole on the anterior, posterior, posterior-lateral, or lateral side can be provided for receiving a threaded arm of an insertion tool.

In another embodiment, the implant has an interior space for receiving an osteoconductive material to promote the formation of new bone.

In another embodiment, the implant is made of a plurality of interconnecting sections with mating sections. Preferably, the implant is made in two halves: a top portion having a top connecting surface and a bottom portion having a bottom connecting surface. The top connecting surface mates with the bottom connecting surface when the top and bottom portions are joined. The top and bottom portions have holes that align for receiving a pin to secure the top and bottom portions together. The pin can be made of allogenic bone.

In a different embodiment, the medial side of the implant has a scalloped edge such that when a first implant is implanted with a second implant with the medial sides facing each other, the scalloped edges define a cylindrical space.

The present invention also relates to a discrete spacer used in conjunction with any of the other embodiments of the implant. The spacer comprises a piece of allogenic bone conforming in size and shape with a portion of an end plates of the vertebrae and has a wedge-shaped profile with substantially smooth top and bottom surfaces. The intersecting regions between the top and bottom surfaces and at least one of the lateral sides and the intersecting regions between the anterior and posterior sides and the same lateral side are curved surfaces to facilitate implantation of the spacer. Thus, the spacer can be implanted through an opening on one side of the spinal canal and moved with a surgical instrument to the contralateral side.

BRIEF DESCRIPTION OF THE DRAWINGS

Preferred features of the present invention are disclosed in the accompanying drawings, wherein similar reference characters denote similar elements throughout the several views, and wherein:

FIGS. 1G to 1I show perspective views of bone portions that may be combined to form an embodiment of an implant of the present development;

FIG. 7A shows perspective views of concentric rings formed of bone material for coupling to form an implant;

FIG. 7B shows a side view of an embodiment of the present invention with an implant formed from the concentric rings of FIG. 7A;

FIG. 7C shows an exploded, perspective view of the implant of FIG. 7B;

FIGS. 8A and 8B show exploded, side views of another embodiment of the present invention forming a spacer;

FIGS. 8C and 8D show additional side views, respectively, of bone pieces of the spacer of FIGS. 8A and 8B;

FIG. 8E shows a side view of the teeth used in the spacer of FIGS. 5A and 8B;

FIG. 15 shows a perspective view of an embodiment of the present invention formed with a cancellous body and cortical struts;

FIG. 16 shows an exploded, perspective view of an additional embodiment of the present invention formed with a cancellous body and cortical struts;

FIG. 17 shows an exploded, perspective view of an additional embodiment of the present invention formed with a combination of cancellous and cortical bone;

FIG. 18 shows a perspective view of an additional embodiment of the present invention formed with a combination of cancellous and cortical bone;

FIGS. 19A and 19B show perspective views of the formation of a composite implant by molding;

FIG. 28 is a perspective view of another embodiment of the implant;

FIG. 29A is a side view of one embodiment of the teeth on the implant;

FIG. 29B is a side view of a second embodiment of the teeth of the implant;

DETAILED DESCRIPTION OF THE PREFERRED EMBODIMENTS

Figure 1A:
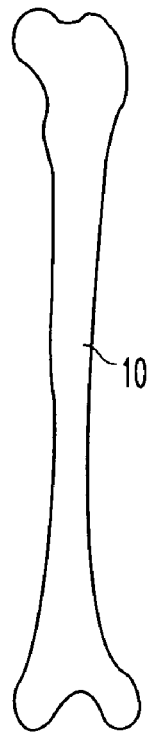
FIGS. 1A to 1D show prior art exemplar bone sizes and shapes for bones from an adult human.
Figure 1B:
Figure 1C:
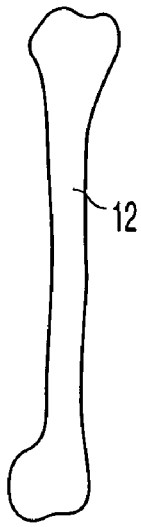
Figure 1D:
Figure 1E:
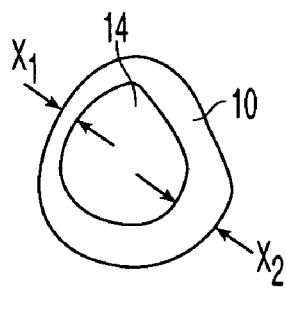
FIGS. 1E–1F show prior art exemplar bone sections having varying wall thickness, the sections taken transverse to the longitudinal axis of the bones.
Figure 1F:
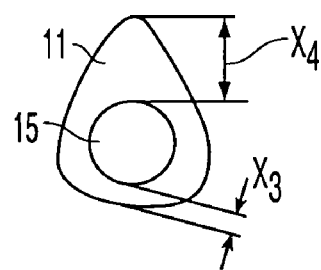

Any of a wide variety of different implant structures, particularly allograft, autograft, and/or xenograft implant structures, can be prepared according to the teachings of the present invention. While a representative selection of implant structures are described and depicted herein, additional disclosure is found in U.S. Provisional Application No. 60/191,099 filed Mar. 22, 2000, which is hereby incorporated herein in its entirety by reference, including all figures.

The present invention allows a more efficient use of bone sections, by permitting those sections that would otherwise have been rejected due to insufficient wall thickness to instead be incorporated in a composite bone section. The composite implant is created by taking two or more bone sections and combining them to create a greater wall thickness. Some or all of the natural shape of each bone may be retained. Furthermore, the composite may be formed of a shape appropriate for implantation, or instead may be formed of a shape that is suitable as bone stock for eventual fashioning into a particular implant or forms.

As used in the description of the present invention, the words fitting, interfitting, mating, locking, interlocking, meshing, and interlacing are all used generically to describe the joining of bone sections or pieces together. Thus, these words are not limited to the use of any particular manner of joining. Thus, for example, the press-fitting of one bone section within a cavity formed in another bone section may be described using any of the above-mentioned terms. In addition, although various preferred mechanical fastening approaches are described, the present invention allows the use of any mechanical device for joining two or more separate parts of an article or structure. Such mechanical devices include, but are not limited to the following: screws, keys, pins, pegs, rivets, cotters, nails, spikes, bolts, studs, staples, bosses, clamps, clips, dowels, stakes, hooks, anchors, ties, bands, and crimps. Also, bonding agents or other chemical means for joining two separate parts may be employed alone or in combination with the mechanical devices. Thus, as appropriate, the means disclosed herein for fixing bone sections to each other may be substituted, as with the above-mentioned mechanical devices, bonding devices, or chemical means. Furthermore, although particular types of joints are disclosed, the present invention is directed to the creation of implants that may be joined using other joints.

While the present invention is preferably directed to the creation of implants from allograft material, the present invention may also be applied to implants that utilize other materials, including but not limited to the following: xenograft, autograft, metals, alloys, ceramics, polymers, composites, and encapsulated fluids or gels. Furthermore, the implants described herein may be formed of materials with varying levels of porosity, such as by combined bone sections from different bones or different types of tissue having varying levels of porosity. For example, cancellous bone is available in a range of porosities based on the location in the body from which the bone is harvested. Extremely porous cancellous bone may be harvested from various areas such as the iliac crest, while less porous bone may be harvested from areas such as a tibial condyle. Thus, the materials properties—particularly the porosity—of the bone components may be selected to meet the needs of a given application.

Cancellous bone components may be attached to syringes or aspirators, and blood or other fluids such as bone-growth inducing substances may be drawn into the plugs. The use of mechanically applied pressure, such as with aspiration devices, permits a greater degree of fluid absorption and/or concentration to be achieved than otherwise readily obtainable by soaking bone in such fluids without applying pressure from a device. In embodiments of the present invention that include hollow regions, a plug of cancellous bone formed using the aforementioned technique may be inserted therein. Alternatively, the plugs may be soaked in a suitable fluid.

Also, the implants described herein may be formed of bone materials with varying mineral content. For example, cancellous or cortical bone may be provided in natural, partially demineralized, or demineralized states. Demineralization is typically achieved with a variety of chemical processing techniques, including the use of an acid such as hydrochloric acid, chelating agents, electrolysis or other treatments. The demineralization treatment removes the minerals contained in the natural bone, leaving collagen fibers with bone growth factors including bone morphogenic protein (BMP). Variation in the mechanical properties of bone sections is obtainable through demineralization. Advantageously, use of a demineralizing agent on natural bone transforms the properties of the bone from a stiff structure to a relatively pliable structure when it is hydrated. Some portions of interfitting bone components may be demineralized in order to achieve improved interfitting. For example, a tissue form may include two bone components having portions that are coupled together with an interference fit. The interference fit may be enhanced if the surface region of one or more of the components is demineralized so that it is pliable and exhibits some elasticity and/or malleability.

In addition, while many of the embodiments described herein show bone components disposed at right angles, or joints formed with right angles, angles that are greater or less than ninety degrees may alternatively be used in implants of the present development.

FIG. 1G shows a first embodiment of implant 16 having an outer sheath 17, an intermediary sheath 18, and a core 19. It should be noted that while bone sections described herein are referred to as sleeves, these components need not be cylindrical or otherwise symmetrical. In this embodiment, outer sheath 17 is a bone section, for example of a femur, that has the outer surface or contour naturally found on a femur. Thus, the outer surface 20 of outer sheath 17 does not require machining and is not machined. The inner surface 21 of outer sheath 17 has been machined to a particular configuration so that intermediary sheath 18 fits within outer sheath 17. Alternatively, as shown in FIG. 1H, implant 16 may have a through hole 22 instead of a core 19, creating a cavity in implant 16. If a through-hole is provided instead of core 19, a hollow implant may be created and bone growth materials such as bone materials in the form of chips, slurries, or fibers, as well as bone inducing substances can be provided therein. While the cavity may be formed from sleeves with two open free ends, such a hollow region may also be created by incorporating one or more sleeves with one free end closed. It should be noted that two or more sections of bone are used to create the composite, and thus there is no limit to the number of sheaths or bone sections that may be combined. Typically, insert or core 19 is cylindrical in shape, as shown in FIG. 1I, and may be made of cancellous bone while each surrounding sheath may be made of cortical bone. Alternating layers of cortical and cancellous bone may be used, or several layers of the same type of bone may be used along with a different type of bone.

The components that are used to create implant 16 may all be formed from cortical bone, all from cancellous bone, or a combination of components formed from cortical and cancellous bone. The interfitting of the components may be achieved through a variety of means, including but not limited to the following: pinning, bonding with a suitable bone bonding agent or chemical means, press fitting, threadably engaging (as by helically screwing one component into another), inserting a tapered component into a component with a matching inner surface, twist-locking, or other interlocking means such as will be described in other embodiments. While the present development preferably allows the creation of an implant 16 from all bone material, it is also anticipated that one or more components used to create implant 16 may be formed of non-bone material such as a synthetic or other material.

Figure 1J:
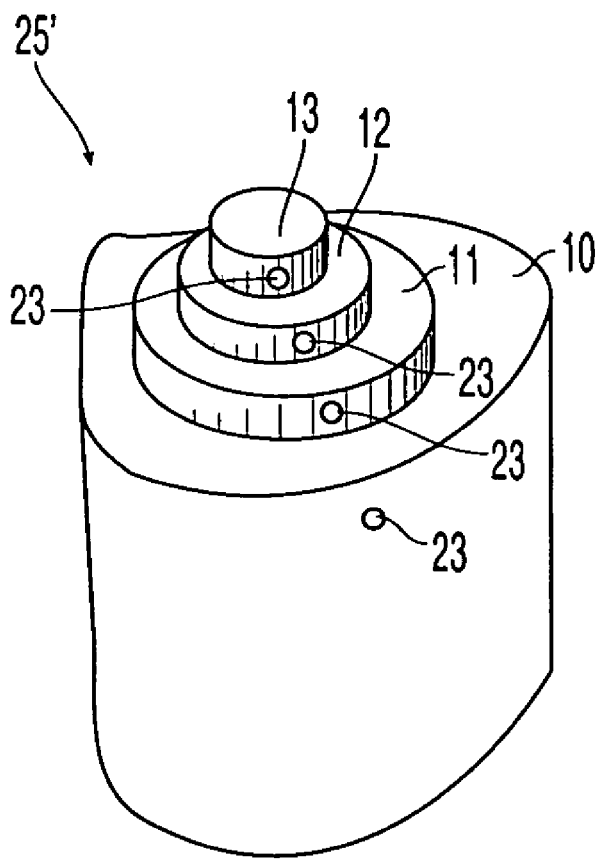
FIGS. 1J to 1K show perspective views of another embodiment of the present development combining multiple bone sections.

As shown in FIG. 1J, in a second embodiment of the present invention many types of bones may be combined in layers to form bone stock 25'. A radius 13 may be encased in humerus sleeve 12, which may be encased in tibia sleeve 11, which may further be encased in femur sleeve 10 that retains the original outer shape of the femur. In alternate embodiments, other bones may be used, such as a fibula or ulna. By machining the inner and/or outer surfaces of each bone section, the bone sections may be inserted into each other with an interfitting relationship. This may result in a strong press-fit, but additional or alternate means of fixation may be employed, such as mechanical means.

The moisture content of the bone sections also may be varied to advantageously permit improved interlocking. Bone sections initially may be provided with moisture content as follows: (1) bone in the natural state fresh out of the donor without freezing, (2) bone in the frozen state, typically at −40° C., with moisture content intact, (3) bone with moisture removed such as freeze-dried bone, and (4) bone in the hydrated state, such as when submersed in water. The expansion and contraction properties that can be obtained from bone during heating, cooling, dehydrating, and hydrating permit an alternate approach to achieving a tight press-fit. In addition, the use of such approaches can provide a tighter press-fit than otherwise obtainable, as well as loosen the manufacturing tolerances required for mating sections of bone.

For example, in the embodiment shown in FIG. 1J, sleeve 12 is initially supplied with a first outer diameter and a first inner diameter. Subsequent freeze-drying of sleeve 12 results in shrinkage such that sleeve 12 assumes a configuration with a second outer diameter that is smaller than the first outer diameter, while having a second inner diameter that is smaller than the first inner diameter. When sleeve 12 is rehydrated or treated with a swelling agent, sleeve 12 may reassume a configuration with the first outer diameter and first inner diameter. By providing a bone section such as a sleeve 12 in the freeze-dried state while disposed inside another bone section such as sleeve 11 that may be loosely interference fit, rehydration of sleeve 12 in place permits a tighter interference fit to be achieved. Notably, a bone section such as core 13 has no inner diameter, and thus such a bone section may shrink in outer diameter only when freeze-dried. Thus, similarly, core 13 may be the bone section that is rehydrated to provide a tighter mating and interference fit with a sleeve 12. Use of these properties can permit greater variation in dimensional tolerance between bone sections during manufacture, while tight final assembly can still be achieved. In addition, protrusions on bone sections become smaller when dehydrated, but expand when rehydrated; in contrast, recesses in bone sections become smaller when hydrated, but larger when dehydrated. Temperature changes may also be used to achieve better interference fits.

Figure 1K:
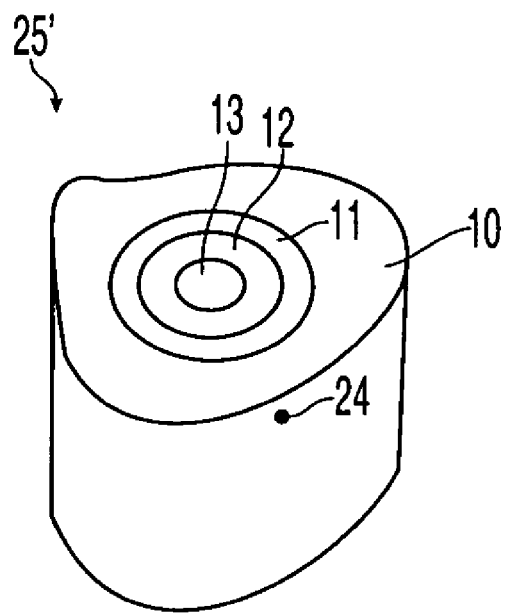

Turning to FIGS. 1J–K, a hole 23 of similar dimension may be created in each bone section, and when the holes are aligned to be coaxial, a pin 24 may be inserted in the holes 23 for fixation. Alternatively, the bone sections may have a slot formed therethrough, similar in orientation to pin 24, and a key can be inserted or press-fitted into the slot to fix the sections with respect to each other. Other bones may also be used, for example an ulna (lower arm) is similar in configuration to radius 13, and thus may be readily substituted. In addition, a fibula can also be readily used in some embodiments, accounting for the size of the bone and any required machining. Also, although the embodiment shown in FIGS. 1J and 1K show bones with generally cylindrical shapes, other shapes can be used, for example by machining the bones to have a rectangular shape or any other shape.

Bone stock 25' is preferably solid, and formed by fitting a smaller diameter bone core within at least one larger diameter sheath. Thus, the availability of precisely machined cores and sheaths permits bone stock 25' to be sized according to the application or anatomy encountered in any given situation. In addition, implants may be constructed from a supply of standardized core and sheath sizes or bone stock sizes so that any required wall thickness can be obtained. The ability to create composite implants of varying sizes has widespread use, particularly in applications such as femoral ring allografts which can benefit from increased wall thicknesses.

In alternate embodiments of bone stock 25', components having non-circular shape may be provided, although not necessarily the natural shape of the original bone. For example, an outer sheath can mate with an inner sheath which has a generally triangular shape, with the inside surface of the outer sheath geometrically conforming to the outside surface of inner sheath. Other polygonal shapes are also contemplated, including parallelograms such as rectangles. In addition, a core may be provided with a shape distinct from both the cylindrical outside surface of the outer sheath and the outside surface of the inner sheath. Thus, the present development permits components with varying outside surface shapes to be interfit to create an implant.

The availability of larger bone stock, as by combining several bone sections, makes it possible to create implants that are properly configured for implantation during a wide variety of procedures. For example, anterior interbody fusion is a surgical procedure which replaces some or all of a disc with a bony graft (implant) by using an anterior approach to the disc. Such a procedure is typically employed in the cervical spine, and implantation of an implant is an effective modality for the treatment of such conditions as degenerative disc disease and herniated nucleus pulposus (slipped disc). Anterior interbody fusion is also used in the lumbar spine in cases of unsuccessful posterior approaches, or in procedures directed to destroyed or damaged facet joints, procedures that combine posterior instrumentation with an anterior discectomy (i.e. removal of herniated disc material from the spinal canal so that the spinal cord or nerve is restored to an unpinched state) and fusion (which allows vertebrae to effectively be knit together into a solid bony mass), along with other procedures that cannot employ a posterior approach. Thus, the implants may also be employed in anterior discectomy and fusion, which involves the removal of an intervertebral disc and the replacement of that disc with an implant that will undergo fusion, both steps being undertaken via an anterior approach. Other surgical procedures employing the anterior approach, including procedures used in fusing the thoracic region, may also make use of the implants.

Alternatively, surgical procedures involving a posterior approach may also employ the implants created using the current invention. For example, posterior lumbar interbody fusion, another surgical technique used for spinal fusion, involves the posterior insertion of an implant into the intervertebral space following posterior excision of a disc through the spinal canal.

Figure 2A:
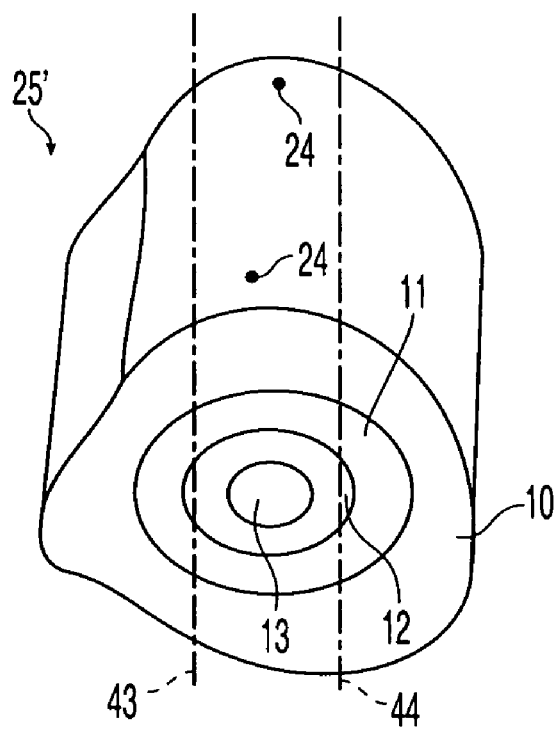
FIG. 2A shows a perspective view of the embodiment of FIG. 1K with section lines.
Figure 2B:
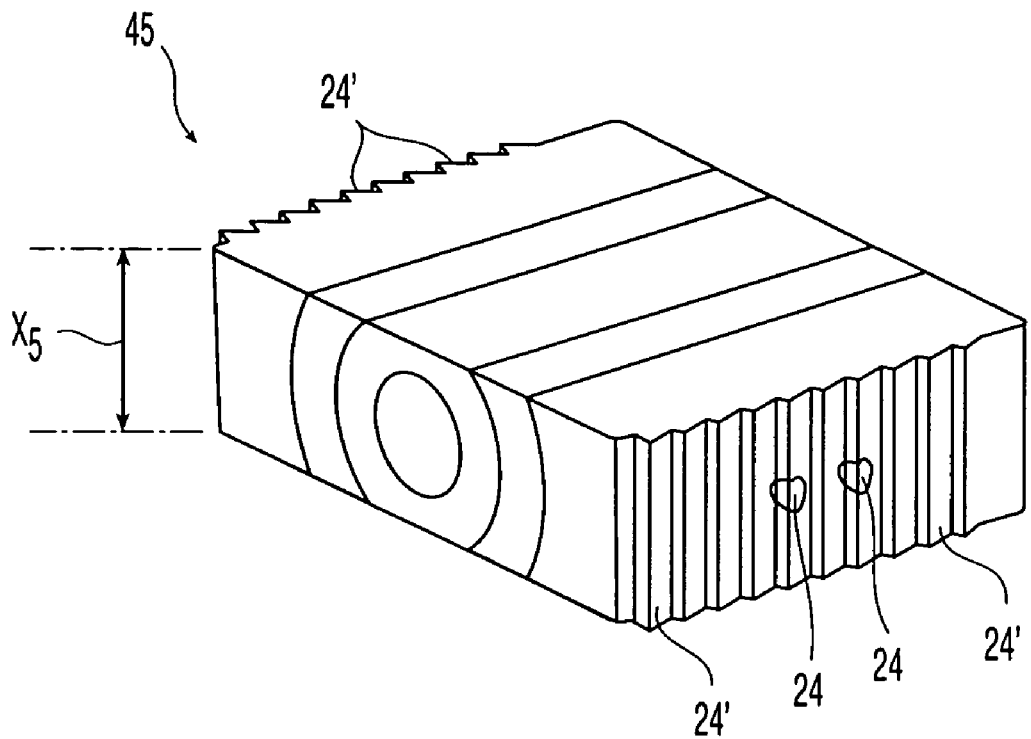
FIG. 2B shows a perspective view of the section of the embodiment of FIG. 1K forming an implant.
Figure 2C:
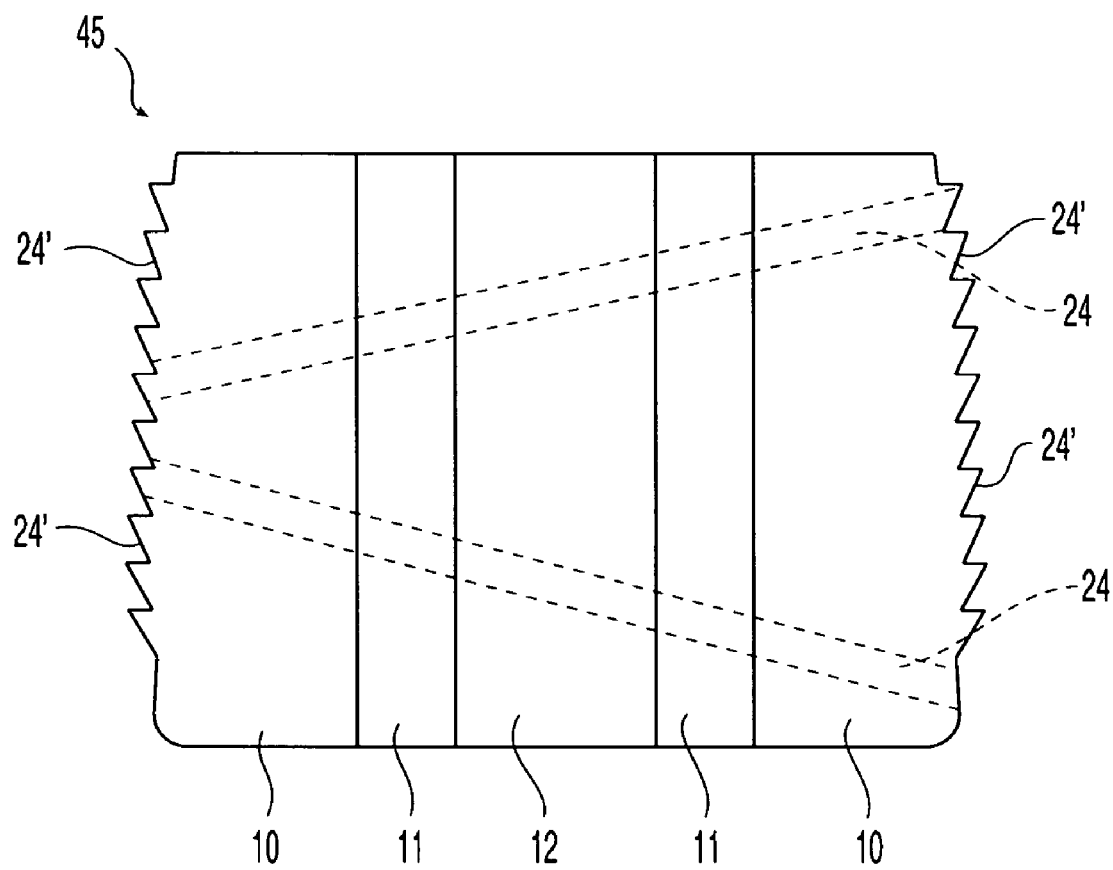
FIG. 2C shows a side view of the implant of FIG. 2B.
Figure 2D:
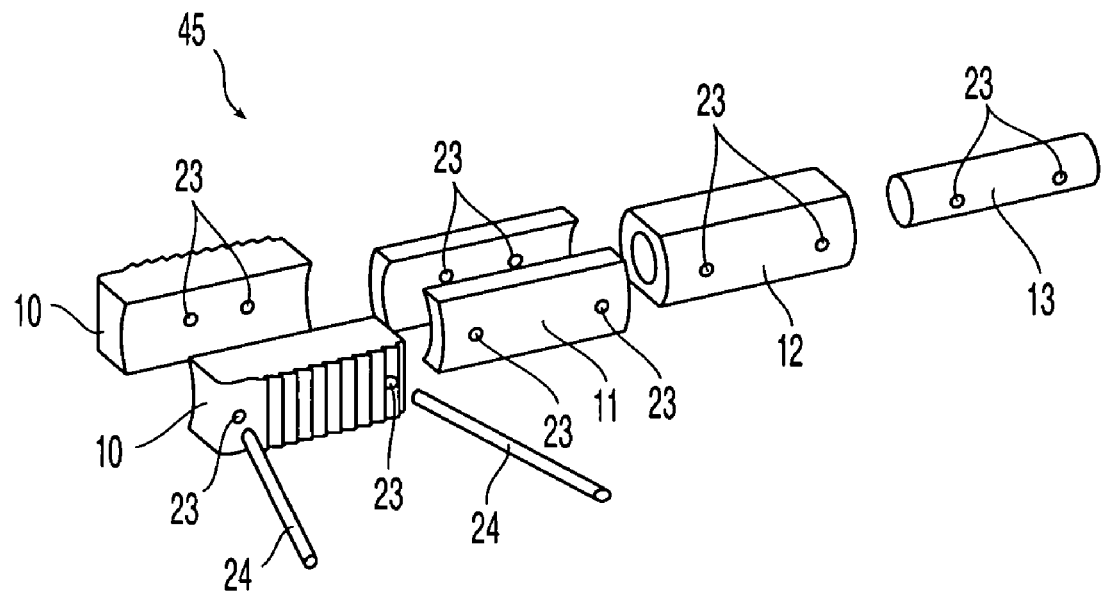
FIG. 2D shows an exploded view of the implant of FIG. 2B.
Figure 3A:
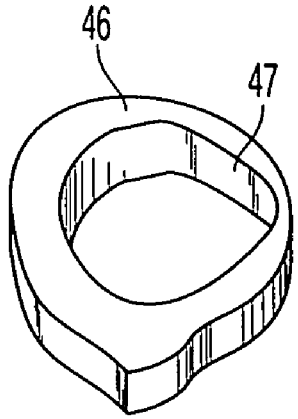
FIGS. 3A to 3C show perspective views of sections of a tibia and femur combined in another embodiment of the present invention.
Figure 3B:
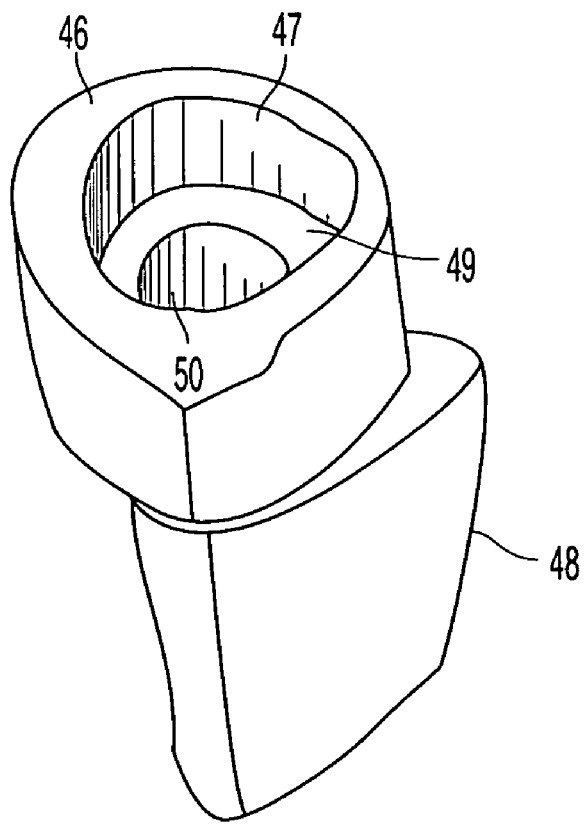
Figure 3C:
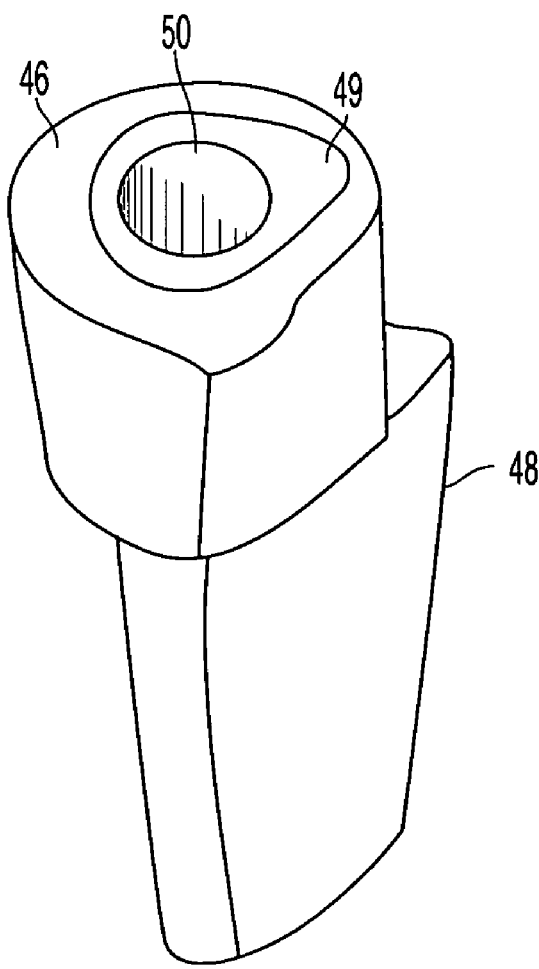
Figure 3D:
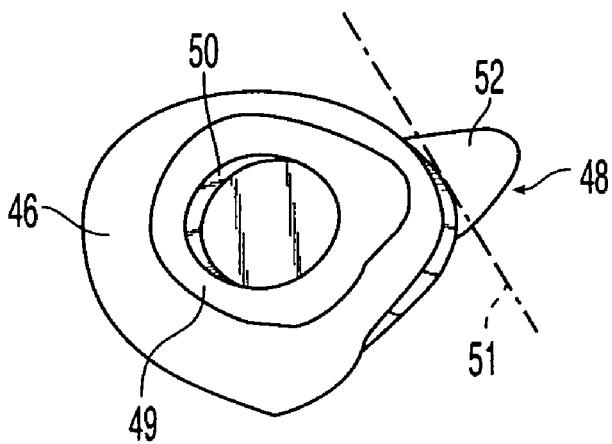
FIG. 3D shows a top view of the embodiment of FIG. 3C.

Bone stock 25' as shown in FIGS. 1J and 1K may be sectioned, for example, as shown in FIGS. 2A–2D, along axes 43 and 44, resulting in a cross-section slice 45 of bone stock 25' having a thickness $X_5$ as shown in perspective view in FIG. 2B and in side view in FIG. 2C. In this embodiment, a pair of pins 24 instead is used to retain the pieces of bones 10, 11, 12, and 13 in engagement. Pins 24 may be oriented at an angle with respect to each other, as shown in FIG. 2C, such that they are nonparallel, thereby resisting separation of the bone pieces. Alternatively, the pieces of bone may be keyed (not shown) for additional interlocking. Such composite bone stock may be used, for example, to create an implant suitable for posterior lumbar interbody fusion. Optionally, in order to prevent migration of such an implant when placed in an anatomical region, serrated regions in the form of saw teeth 24' may be provided on the periphery of slice 45. Although slice 45 includes a core 13 that is fully surrounded by sleeve 12, as shown for example in the exploded view of slice 45 in FIG. 2D, alternate embodiments of a slice of bone stock 25' do not completely surround core 13.

While bone stock 25' utilizes four separate bone pieces, other numbers of pieces are contemplated. For example, a core may be surrounded by only two sleeves to produce a desired stock size. Also, pins 24 may be formed from bone.

Another composite implant is shown in FIGS. 3A–3D. In this embodiment, a section of a femur 46 has an inner surface 47. Preferably, in order to increase the wall thickness of section 46, this bone section may be used as a sleeve that surrounds a portion of a tibia section 48. Although the tibia naturally has a generally triangular shape, a portion 49 of the tibia 48 may be machined to have an outer geometry that mates with inner surface 47 of femur 46. A canal 50 may remain in the composite implant, or it may be filled with another bone or other material. By inserting portion 49 within sleeve 46, a protruding section 52 remains on tibia section 48. Such a section may be cut off, for example along axis 51, so that section 52 may be used for another purpose, such as serving as bone material for use in other implants.

Figure 4A:
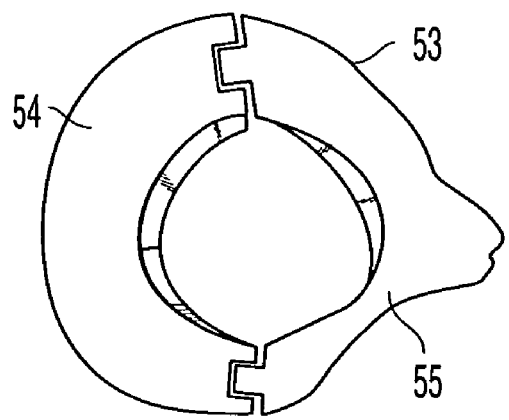
FIGS. 4A to 4D show top views of yet another embodiment of the present invention combining sections of bone having acceptable wall thickness with mating joints.
Figure 4B:
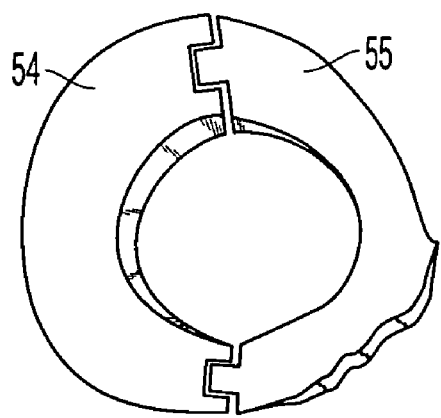
Figure 4C:
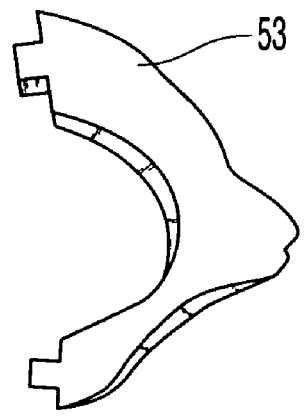
Figure 4D:
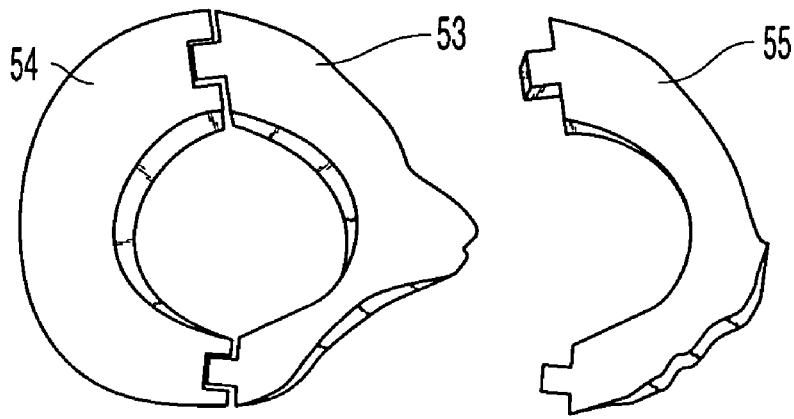
Figure 4E:
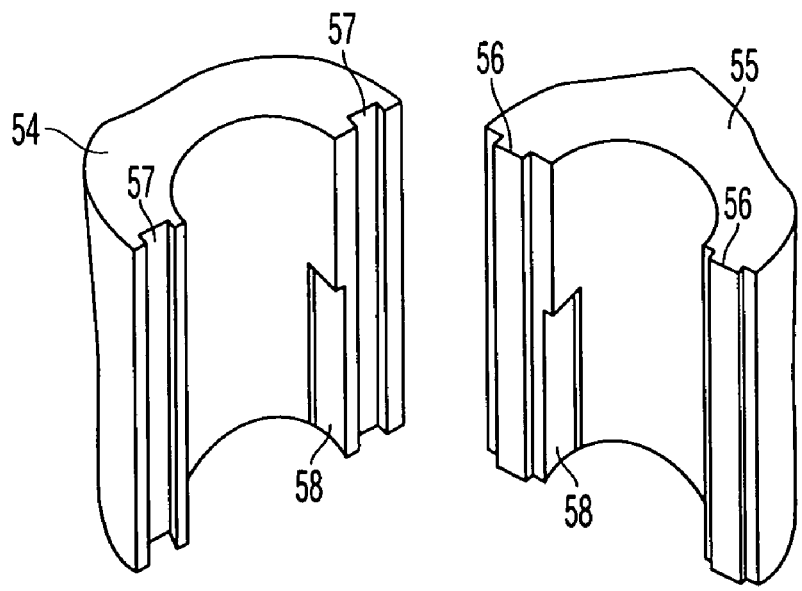
FIGS. 4E to 4G show exploded, perspective views of another embodiment of the present invention combining sections of bone having acceptable wall thickness with mating joints.
Figure 4F:
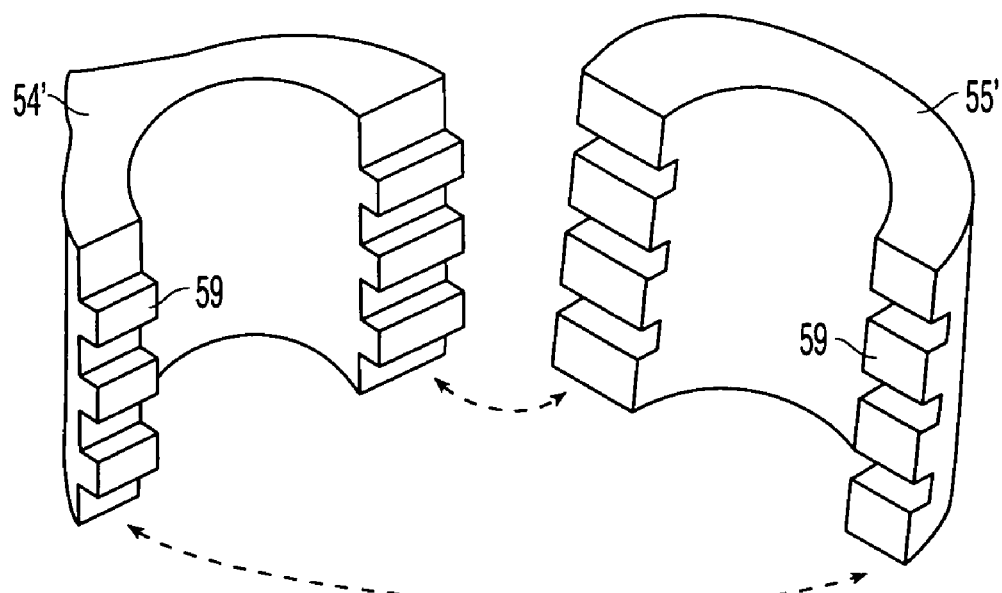
Figure 4G:
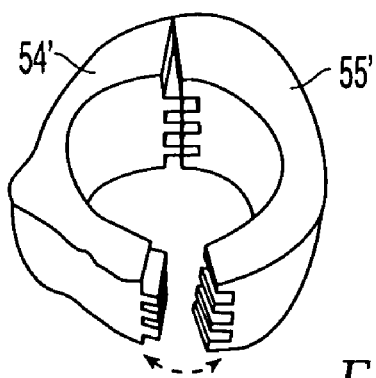

Yet another approach to maximizing the use of a bone sections with thin wall areas is shown in FIGS. 4A to 4D. In this embodiment, a femur section 53 is cut with a tongue and groove pattern, creating a portion 54 having an acceptable wall thickness and a portion 55 with an unacceptable wall thickness. A similar cut is performed on another femur section, and the portion 55 from the second femur section may be removed and matched with the portion 54 from the first femur section. Thus, a composite implant is created with consistently thick and acceptable wall thickness. Portion 53 may be used for another purpose. In addition to matching tongues 56 and grooves 57 formed in sections 55 and 54, respectively, other matching geometrical shapes such as matching notches 58 may also be provided as shown in FIG. 4E. Other suitable configurations of interlocking portions include interlocking teeth 59 formed in matching sections 54' and 55', as shown in FIGS. 4F and 4G. In an alternate embodiment, a synthetic portion may be matched with a bone portion to create a composite implant with appropriate wall thickness, and may be formed of other materials such as metals, polymers, or ceramics.

Figure 5A:
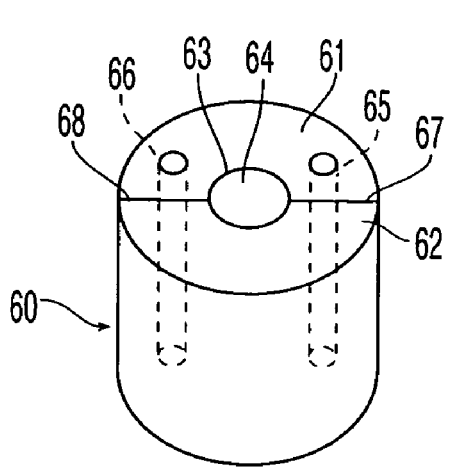
FIGS. 5A to 5E show perspective views of additional embodiments of the present invention combining multiple bone sections.
Figure 5B:
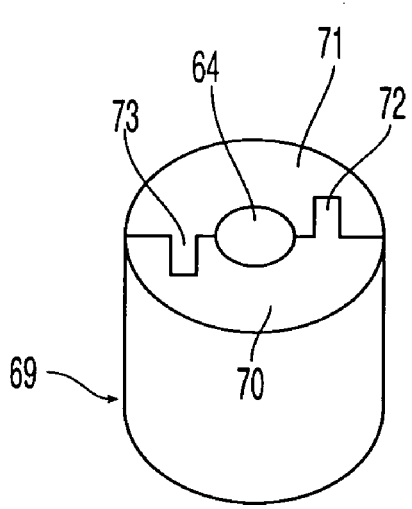
Figure 5C:
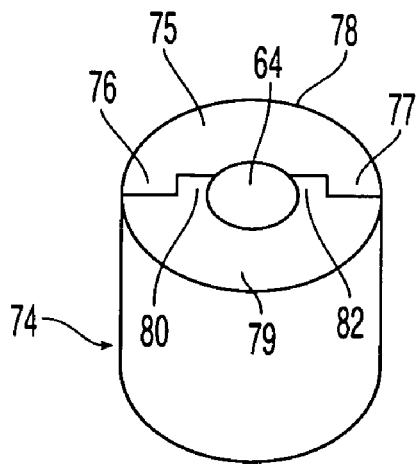

FIGS. 5A to 5C show implants created by joining three components. Implant 60 has two outer portions 61 and 62 that surround the cylindrical surface 63 of core 64. Outer portions 61 and 62 are joined to each other using pins 65 and 66 (shown in phantom), and core 64 is press fit or otherwise secured between portions 61 and 62. In the embodiment shown in FIG. 5A, portions 61 and 62 have mating surfaces defined at areas 67 and 68 that do not interfit. Alternatively, as shown in FIG. 5B, implant 69 has two outer portions 70 and 71 that interfit and surround a core 64. Portion 70 has a tongue portion 72 that fits in a groove in portion 71. Likewise, portion 71 is also provided with a tongue portion 73 that fits in a groove in portion 70. Notably, designs employing tongue and groove configurations have a significantly increased mating surface area, thereby providing a greater surface over which joining can be achieved with concomitantly greater strength.

Figure 5D:
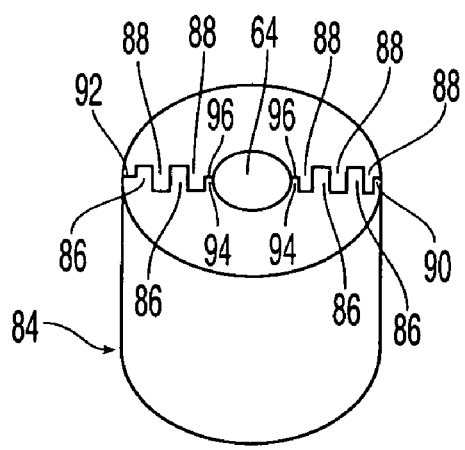
Figure 5E:
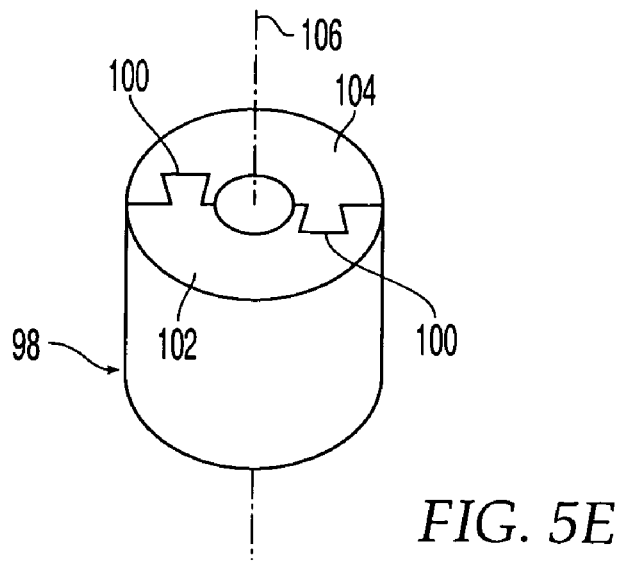

Interfitting may also be achieved using the design of implant 74 shown in FIG. 5C. Portion 75 has protruding portions 76 and 77 that each are partially formed with outside surface 78, while portion 79 has protruding portions 80 and 82 that interfit with protrusions 76 and 77. As shown in FIG. 5D, implant 84 may instead include a combination of tongue portions 86 and 88 that fit within grooves disposed in opposing outer portions, protruding portions 90 and 92, as well as mating surfaces 94 and 96. Implant 98 uses dovetail joints 100 to secure outer portions 102 and 104. The dovetail joint is particularly useful because it resists pullout, although sliding may still occur along axis 106. The dovetails provide a positive lock transverse to axis 106 so that pullout can be prevented, and such an interlocking arrangement of components generally resists the separation of the bone components from each other. As with the tongue and groove design, the use of a dovetail joint creates a greater surface area for bonding. Although implant 98 is shown with only one dovetail on each outer sheath portion, additional dovetails may be provided. Additionally, the present development allows the joining of more than two outer portions. Thus, instead of two halves, three or more outer portions may be joined. Furthermore, the core may be of any desired shape, as may be the outside surface of the outer portions. Portions of the implants, such as portions 75 and 79, may be formed of different materials, for example cortical bone, cancellous bone, and ceramic materials.

Figure 5F:
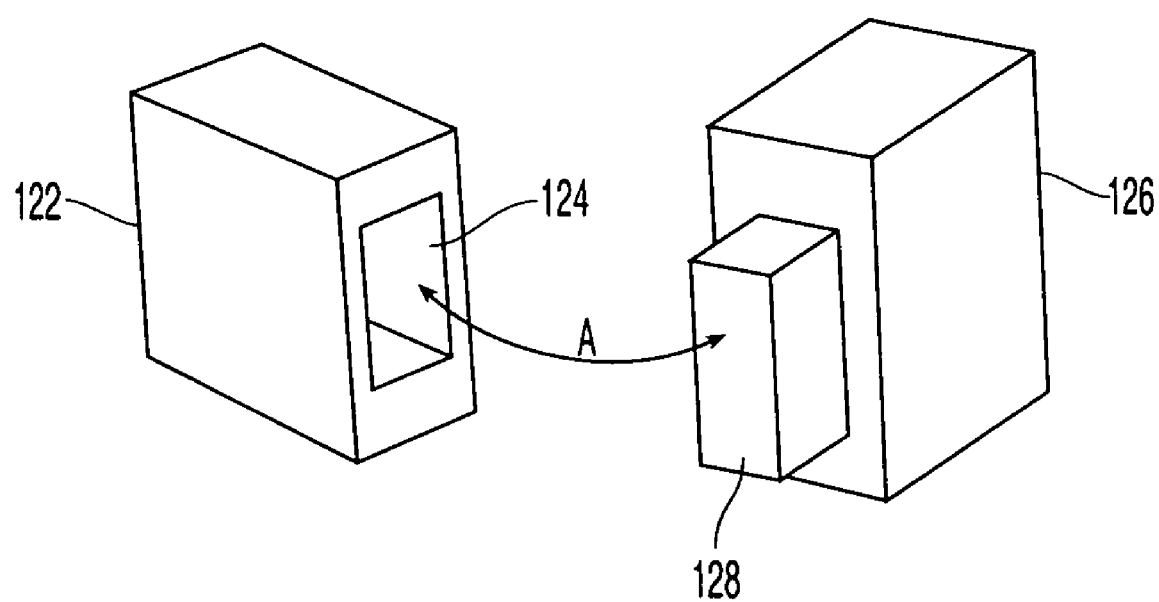
FIG. 5F shows an exploded, perspective view of another embodiment of the present invention combining multiple bone sections.
Figure 6A:
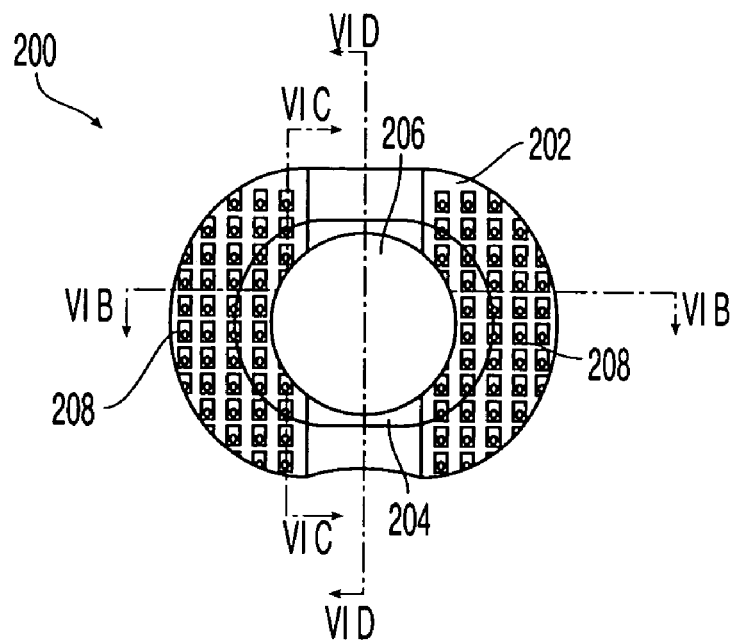
FIG. 6A shows a top view of another embodiment of the present invention forming a femoral ring implant.
Figures 6B, 6C, 6D:
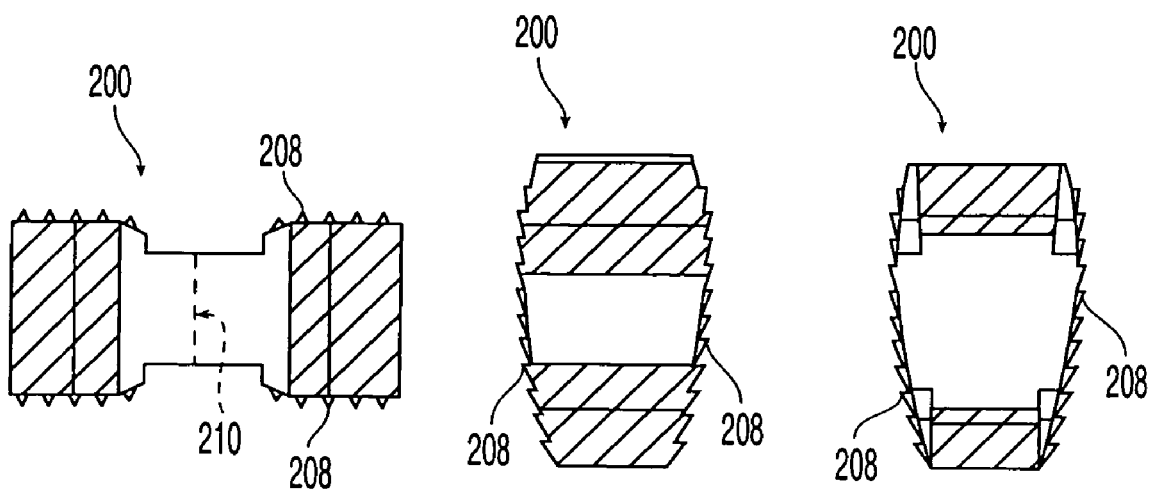
FIG. 6B shows a side view of the implant of FIG. 6A.
FIG. 6C shows a cross-section of the implant of FIG. 6A taken along line VIC—VIC.
FIG. 6D shows a cross-section of the implant of FIG. 6A taken along line VID—VID.

Numerous types of joints are useful in the present development, including joints that permit articulation such as a ball and socket type of joint, and particularly joints that permit firm interlocking between two components to prevent relative movement between the components. Preferably, mortise and tenon joints can be used to interfit multiple bone components to create an implant as shown for example in FIG. 5F. Bone component 122, shown in exemplary form with a rectangular shape, contains a rectangular mortise or cavity 124. Bone component 126, also rectangular in overall configuration, includes a rectangular-shaped tenon 128 that is inserted in cavity 124 to thereby form a joint. The size and shape of tenon 128 is closely matched to that of cavity 124. Once components 122 and 126 are joined, as shown by arrow A, an implant or larger bone stock is created. The mortise may be partial or extend through the component, and a tenon sloped haunch portion may be provided on the tenon for interfitting with a mortise sloped haunch portion on the mortise. Other forms of the mortise and tenon joints are also appropriate, as are other coupling arrangements such as edge joints including tongue and groove joints, rabbeted points, toothed joints, and dovetail joints.

The use of insertable securing elements such as keys, pegs, pins, wedges, or other suitable components in joints to assist in securing bone components to each other is also an effective approach to providing a stable joint. Keys, for example, may be inserted in notched or grooved areas in bone components, serving as the securing element between two or more bone components. Parameters that may be varied when using insertable securing elements, such as keys, include the angle of application, the spacing of the elements, and the thicknesses of the elements.

Referring to FIGS. 6A–6D, a femoral ring implant 200 is shown for use in anterior lumbar interbody fusion, and is formed of several layers of bone in the form of sleeves. In the preferred embodiment, a sleeve 202 formed from a femur or tibia has another sleeve 204 formed from a humerus inserted therein. The sleeves 202, 204 may be press-fit, pinned, keyed, and/or joined by other means. Although implant 200 is shown with a central chamber 206, which may be left empty or filled with bone materials or other bone inducing substances, in alternate embodiments central chamber 206 may be filled with another bone portion to create a solid implant. A cancellous plug, for example, may be placed in central chamber 206. Combinations of cortical or cancellous bone may be used, and additional sleeves may also be provided. Saw teeth 208 or other protrusions may be provided on the periphery of implant 200 to anchor the implant in the desired anatomical region. Implant 200 is formed in a generally kidney-shaped configuration to conform to the natural anatomy of vertebral bodies encountered during anterior lumbar interbody fusion.

Alignment indicia 210 may be provided on the outer surface of implant 200, as with a line or other aid. Preferably, indicia 210 is an imprint, i.e. with ink, although indicia 210 may instead be provided in the form of surface scoring. The indicia suitable for the present invention includes, but is not limited to, markers such as lines, arrows, lettering, and symbols. In addition, alignment indicia 210 preferably is provided on the anterior side of implant 200 to aid in alignment with the natural anatomy encountered during surgery, and particularly to aid in alignment with the anterior longitudinal ligament (ALL) that extends over the length of the lumbar spine anterior to the vertebral bodies. In particular, the ALL may be used as a landmark in combination with alignment indicia 210, for example, to permit a surgeon to properly align implant 200 with respect to surrounding anatomy.

Referring to FIGS. 7A to 7C, interlocking concentric circular bone components may also be created from bone stock. For example, concentric bone portions 1020, 1022, 1024, 1026, and 1028 may be combined to form an implant. Some of the concentric circular components may be provided with two portions, each having a different outer diameter such as portion 1047 and ridge 1048. Ridge 1048 has an outer diameter that is slightly smaller than the inner diameter of ridge 1049, thus allowing ridge 1048 of a first component to be press fit into the ridge 1049 of a second component. This permits implants of varying sizes to be created by interlocking several bone components together, for example to create implant 1050. Side and exploded, perspective views of implant 1050 are shown in FIGS. 7B and 7C respectively. Keys may also be inserted into the walls of assembled bone components to provide further interlocking of the concentric cylinders. Furthermore, once assembled and secured to each other, the annular members may be cut to create other appropriate shapes. Implant 1050 utilizes bone portions that are formed from the natural size and overall geometry of particular bones, so that available bone material may be used efficiently. For example, bone portions 1020, 1028 may be formed from a radius, bone portions 1022, 1026 may be formed from a humerus, and bone portion 1024 may be formed from a femur. Although implant 1050 is shown with concentric circular portions, is other embodiments non-circular, ring-shaped bone components may also be similarly provided such as oblong arcuate forms like elliptical shapes, or polygonal shapes. In some embodiments, caps are optionally provided in the outermost concentric circle bone portions to form a completely-enclosed chamber within implant 1050.

Turning to FIGS. 8A–E, another spacer implant 1100 according to the present invention is shown. Two bone pieces 1102, 1104 are provided with mating portions 1107, 1108 respectively. Once interfitted, bone pieces 1102, 1104 provide a multi-layer, oval-shaped implant structure with a central hole 1112, which may be packed with bone-growth inducing substances. Preferably, one or more of the outer surfaces on implant 1100, such as outer surface 1106, is provided with teeth 1110. In a preferred embodiment, teeth 1110 are pyrimidal in shape with edges formed at an angle β of about 60°. Preferably, at least a portion of an inner surface of a bone piece 1102, 1104 is provided with a protrusion that is received in an opposing groove. For example, as shown in FIGS. 8A and 8B, bone piece 1102 is provided with an inner surface that includes a groove 1118 for mating with a symmetrically formed protrusion 1116 on bone piece 1104. Centering lines 1114, 1116 may also be provided on implant 1100 to assist in the orientation and overall placement of implant 1100 in the body. Although the implant 1100 of FIGS. 8A–E is formed of two layers of bone, implants of more than two layers of interfitting bone are contemplated.

Figure 9A:
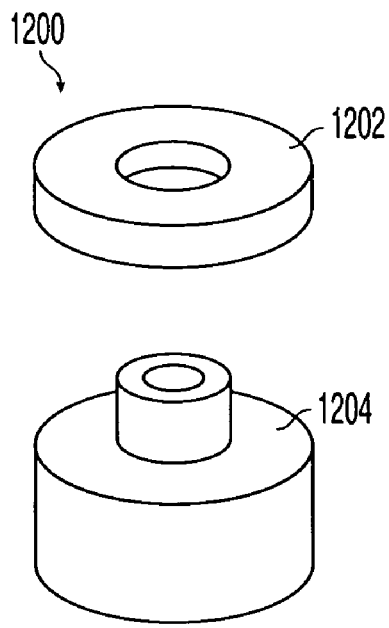
FIGS. 9A to 9C show exploded, perspective views of additional embodiments of the present invention using washer-shaped bone portions.
Figure 9B:
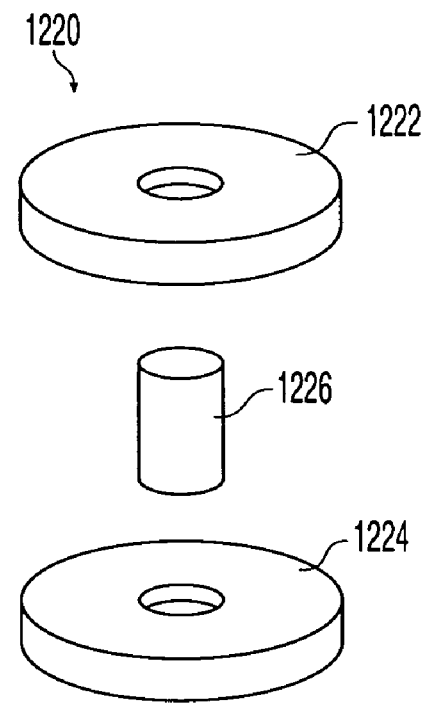
Figure 9C:
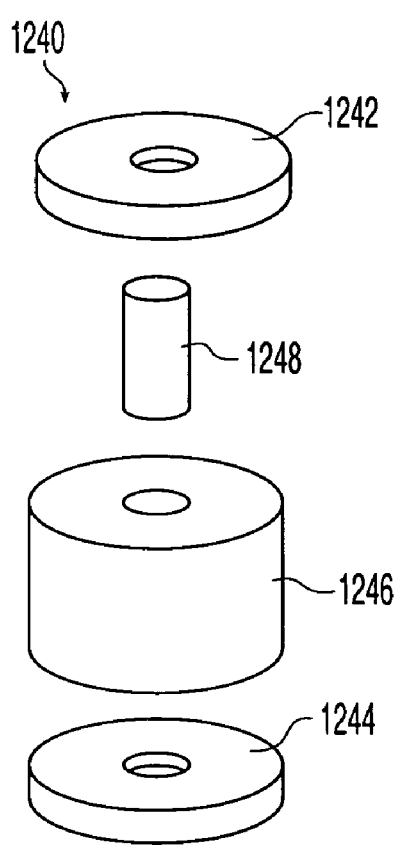

Referring to FIGS. 9A–C, various other configurations of bone portions may be provided. For example, an implant 1200 may be formed with interfitting washer 1202 and base 1204 bone pieces. Alternatively, an implant 1220 may be formed with multiple washer-like pieces 1222, 1224 that interfit with a core 1226. In addition, an implant 1240 may be formed with washer-like pieces 1242, 1244, an intermediate piece 1246, and a core 1248 that extends the length of all pieces 1242, 1244, 1246. The mating surfaces of the components of these embodiments may be fixed to each other using any of the aforementioned means such as pins and adhesives. In addition, different types of bone may be selected for the components of these embodiments. In one embodiment, implant 1200 includes a cancellous ring 1202 and a cortical base 1204. In another embodiment, implant 1240 includes cortical washer-like pieces 1242, 1244, a cancellous intermediate piece 1246, and a cortical core 1248.

Figure 10:
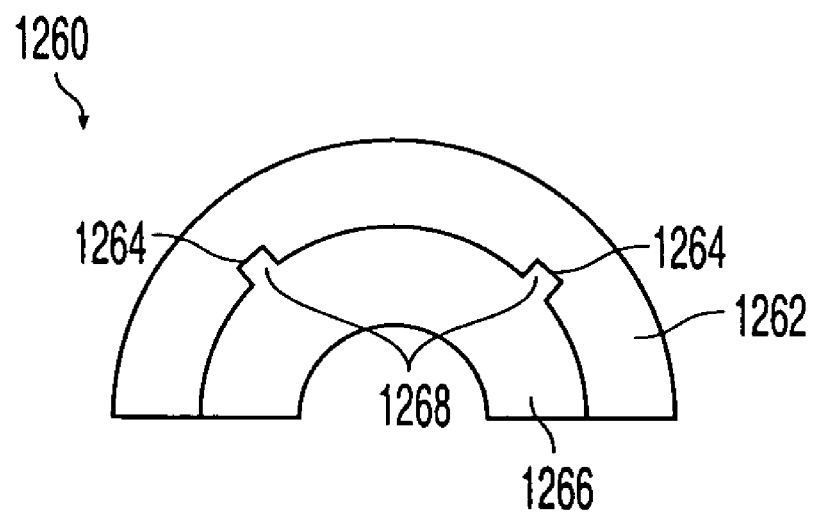
FIG. 10 shows a top view of an additional embodiment of an implant according to the present invention with bowed bone portions.

Another embodiment according to the present invention is shown in FIG. 10. Implant 1260 is formed with bowed bone portions 1262, 1266. Bone portion 1262 is provided with grooved regions 1264, while bone portion 1266 is provided with protrusions 1268 that mate with grooved regions 1264.

Figure 11:
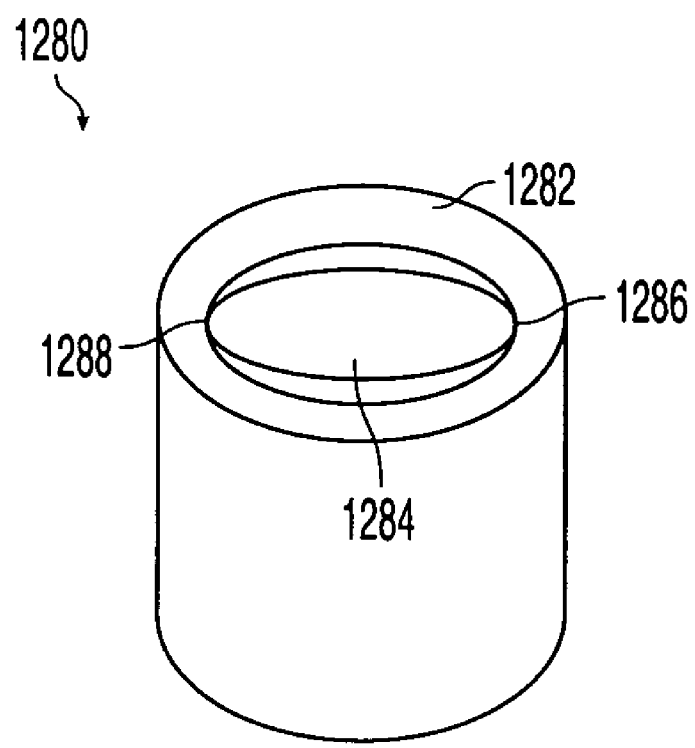
FIG. 11 shows a perspective view of an additional embodiment of an implant according to the present invention with press fitting of bone portions in two locations.

Yet another embodiment of an implant 1280 is shown in FIG. 11. An outer bone portion 1282 surrounds an inner bone portion 1284. Advantageously, inner bone portion 1284 only contacts outer bone portion 1282 along two small regions 1286, 1288 along the length of portions 1282, 1284. Thus, in this embodiment a press-fit of bone portions 1282, 1284 is only provided at regions 1286, 1288. Such a construction permits outer bone portion 1282 to deflect with respect to inner bone portion 1284. Such a construction facilitates press-fitting of outer and inner bone portions. Closely mating outer and inner bone portions may be difficult to press-fit due to the tightness inherent in the fit itself and the dimensions of the bone portions. A less tight fit, as provided for example by implant 1280, may permit a press-fit to be achieved with less difficulty. In sum, an implant 1280 with an inner bone portion 1284 of oblong or slightly elliptical geometry can provide an acceptable interference fit, while facilitating assembly without as much concern for breakage. While a press-fit with two points or regions of contact has been described, it is also contemplated that press-fits with more than two points or regions of contact may be used.

Figure 12:
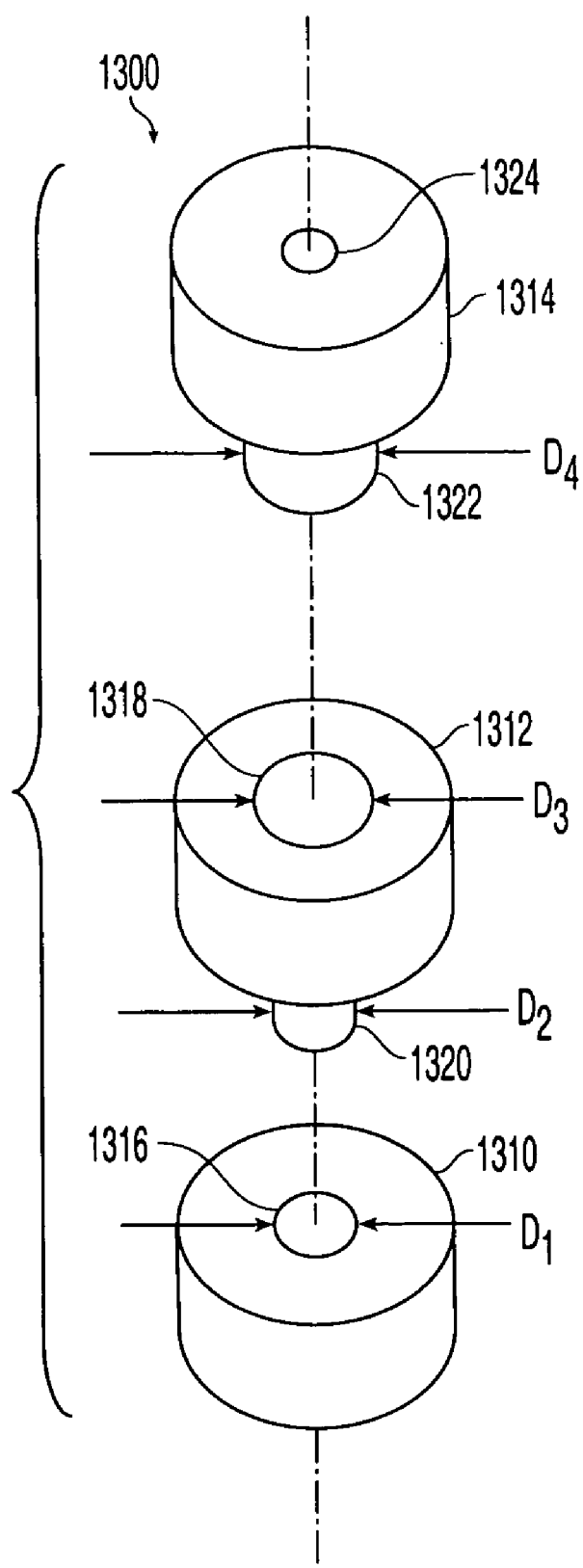
FIG. 12 shows an exploded, perspective view of an additional embodiment of an implant according to the present invention with bone portions that mate.
Figure 13:
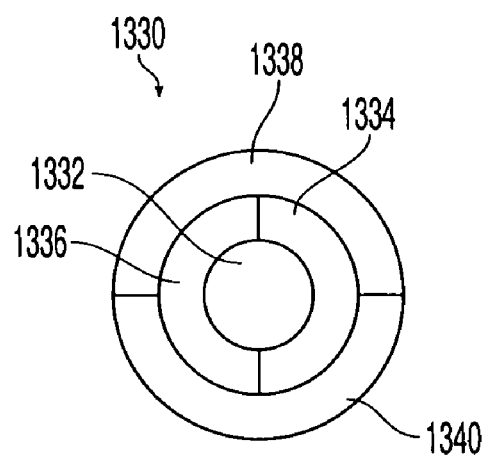
FIG. 13 shows a top view of an additional embodiment of a multilayer implant according to the present invention.
Figure 14:
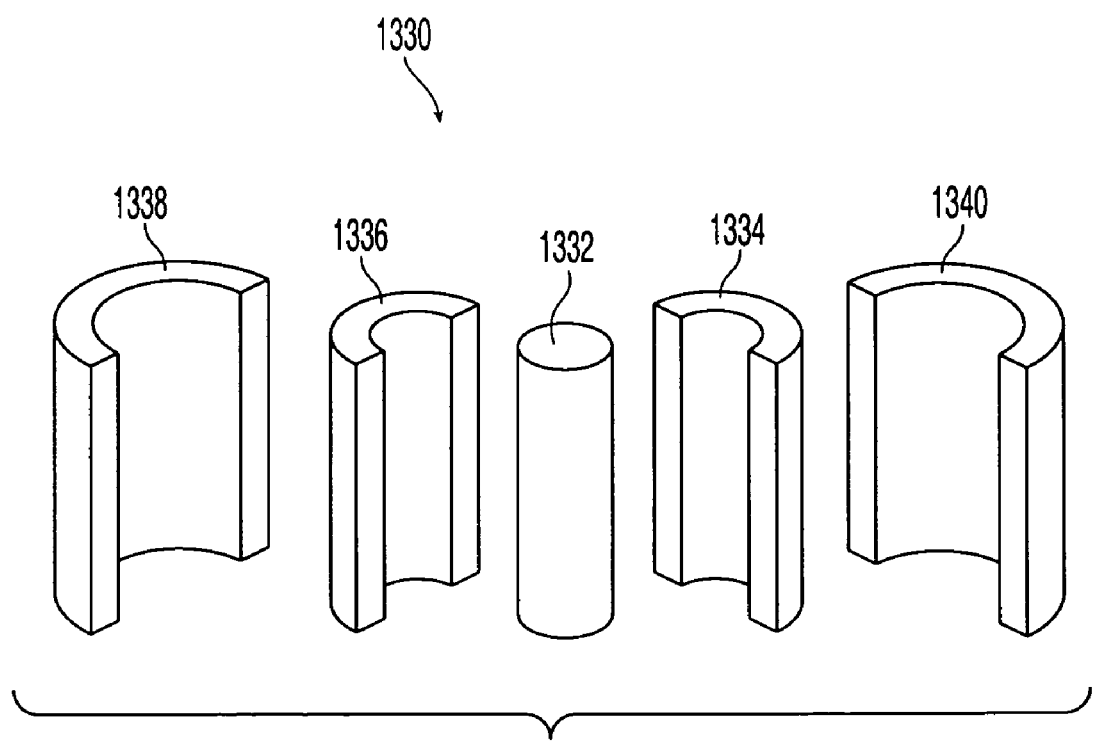
FIG. 14 shows an exploded, perspective view of the implant of FIG. 13.

Further embodiments of multipiece implants are shown in FIGS. 12–14. Referring to FIG. 12, implant 1300 is formed of bone portions 1310, 1312, and 1314. Bone portion 1310 includes a central hole or recess 1316 with a diameter $D_1$, while bone portion 1312 includes a prong 1320 with a diameter $D_2$ and a central hole or recess 1318 with a diameter $D_3$. Diameters $D_1$, $D_2$ are chosen such that bone portions 1310 and 1312 mate at hole 1316 and prong 1320, and preferably a press-fit is achieved. Similarly, bone portion 1314 includes a prong 1322 with a diameter $D_4$ and a central hole or recess 1324. Diameters $D_3$, $D_4$ are chosen such that bone portions 1312 and 1314 mate at hole 1318 and prong 1322, and preferably a press-fit is achieved. In the embodiment shown, diameters $D_2$, $D_4$ are chosen to be different. Thus, if an implant requires a central cancellous bone portion 1312 between cortical bone portions 1310, 1314, the proper construction is more likely to be achieved due to the specific interfitting relationships of the bone portions.

As shown in FIGS. 13–14, a multi-layer implant 1330 includes a core bone portion 1332 surrounded by bone portions 1334, 1336, 1338, 1340. The shape of core bone portion 1332 serves as a key for orienting and mating with bone portions 1334, 1336, and similarly bone portions 1334, 1336 together serve as a key for orienting and mating with bone portions 1338, 1340. Any number of bone portions may be aligned with respect to each other using this key configuration.

Referring now to FIGS. 15–16, the use of cortical bone struts to confer additional structural strength to implants is shown. For example, implant 1350 of FIG. 15 includes a cancellous body 1352 with holes 1353 formed therein. Cortical struts 1354 are inserted in holes 1353 to improve the strength of implant 1350. In particular, because cancellous bone does not provide significant structural strength, cortical struts with higher structural strength, particularly in compression, are used. Advantageously, implant 1350 is formed in part from an osteoconductive material, the cancellous bone, to facilitate incorporation of the implant into surrounding bone tissue. Implant 1350 may be formed of bone that is demineralized, partially demineralized, or with natural mineral content, and may be formed from other shapes. Holes 1353 and struts 1354 may have other cross-sections such as triangular or rectangular shapes, and similarly body 1352 may be another shape. A central hole 1355 also may be included and additional materials may be packed or molded therein. Turning to FIG. 16, an exploded view of an implant 1360 is shown. Implant 1360 includes cortical end caps 1362, 1364 disposed on opposing sides of body 1368. Cortical struts 1366 extend through holes 1370 in body 1368 to improve structural integrity of the implant. One or both of end caps 1362, 1364 may include holes or recesses, such as holes 1372 as shown in end cap 1364, to receive portions of struts 1366. The struts may be pressfit within holes 1370, 1372. Cortical end caps 1362, 1364 also serve to distribute loading on implant 1360.

Additional embodiments of implants with combinations of cortical and cancellous bone are shown in FIGS. 17–18. Implant 1380 includes opposing cortical caps 1382 each with heads 1384 and protrusions 1386. Cancellous body 1390 includes opposing recesses or holes 1390, which receive protrusions 1386 of caps 1382. Implant 1392 includes cortical shells 1394, 1396 with a cancellous body 1398 disposed therebetween. A central region 1399 may be empty, filled with a plug of bone material such as cancellous bone, or filled with other materials.

Implants may be formed from composites of bone material and material that is molded thereto. For example, femur section 46 shown in FIG. 3A has an inner surface 47 that conforms to the natural shape of the femur bone canal. The wall thickness of femur 46 varies, and may be increased using several approaches. As shown in FIGS. 19A and 19B, a molding apparatus 1400 may be used to produce an implant 1410 with desired wall thickness. A mold 1402 or object of smaller dimension than the hole 1404 defined by inner surface 47 of femur section 46, and a curable liquid, slurry, paste, or gel such as bone cement, a viscous polymer, or a ceramic slurry can be poured between mold 1402 and inner surface 47 and allowed to set in place. Alternatively, or in addition, a mold 1406 with a larger dimension than femur section 46 may be placed around it. The wall thickness of femur section 46 may be increased by pouring bone cement between mold 1406 and outer surface 1408, so that the bone cement extends from the top surface 1407 to the bottom surface 1409. In alternate embodiments, the bone cement may not extend to top surface 1407.

Once the bone cement has set, molds 1402, 1406 may be removed, leaving a tissue form 1410 with a composite wall of the original femur section 46 and bone cement sections 1412, 1414. Other filler materials can be used with molds 1402, 1406, such as a mixture of hydroxyapatite and cement that sets in place. In alternate embodiments, materials are molded only to portions of bone sections, instead of being molded to completely surround inner and/or outer surfaces of bone sections. Additional molds can be used for surrounding adjacent bone sections in implants formed with multiple pieces of bone, thereby permitting multiple bone sections to be coupled together with an intermediary layer of bone cement.

Molded sections such as sections 1412, 1414 may include mixtures or suspensions of cancellous and/or cortical bone powder, bone chips, and bone fibers, in natural or demineralized conditions, in combination with bonding agents such as bone cements, water, fat, blood, thrombin, and fibrin. The fibers, in particular, may be oriented to provide particular mechanical properties. For example, fibers may be oriented generally parallel to axis 1416, transverse to axis 1416, or in mixed orientations in order to achieve desired strength when encased in bone cement that is cured. Other materials also may be combined with bonding agents or other carriers, such as hydroxyapatite. Furthermore, sections 1412, 1414 may additionally be formed by applying pressure while curing occurs.

Alternatively, compactable powders and/or fibers of various sizes and shapes may be pressed and compacted in place, without bonding agents or with minimal use thereof. Such pressed structures may be further encapsulated in thin layers of bone cements or polymers such as biodegradable polymers. While loose powder of varying particle sizes may be compressed and densified to produce a compact of the powder, it is difficult to apply uniform pressures while producing the compact. The so-called "single action" pressing technique, which typically applies a force to the powder in a single direction, may be used in the present invention. However, in some embodiments, because it is desirable to produce a compact with a more uniform density throughout the structure, other pressing techniques may be used.

Furthermore, the components of the implants described herein may be formed by molding various materials onto support structures such as meshes or other structures that are known to one skilled in the art. For example, titanium mesh indicated for reinforcement of bony regions in orthopedic procedures is typically available in preformed round and oval-shaped cylinders. The metal mesh may be encapsulated or otherwise surrounded by another material such as bone powder or bone fiber impregnated bone cement that has dried in place around the mesh. Multiple bone components may be interfitted together and further encapsulated or otherwise surrounded by molded materials for additional reinforcement. Also, molded material may be used to further couple two or more pieces of bone together. For example, a polymer such as polymethylmethacrylate may be placed in the central chamber of an implant and allowed to cure in place.

Figure 20:
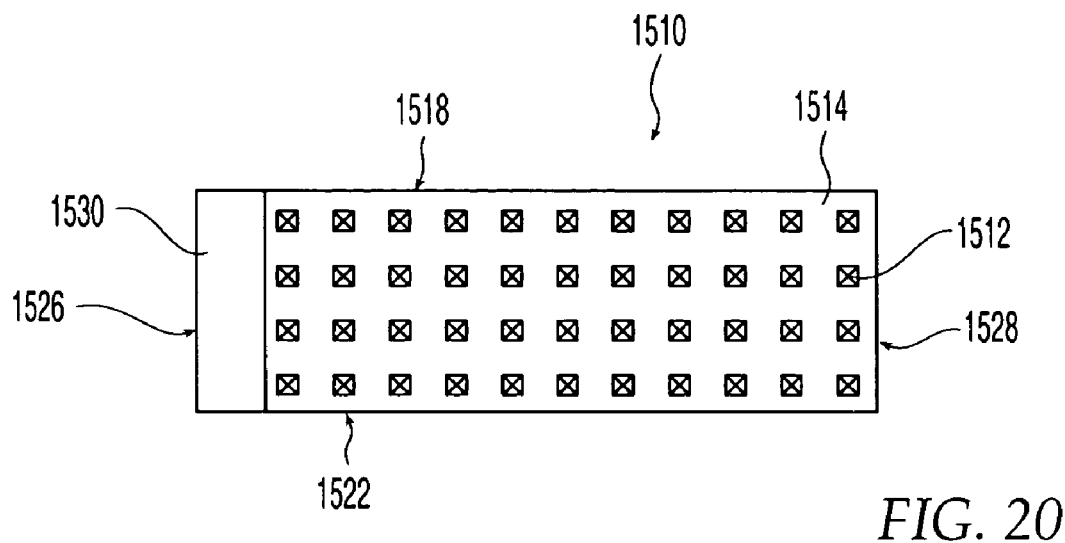
FIG. 20 is a top view of a another embodiment of an implant according to the present invention.

Turning now to FIG. 20, a top view of an embodiment of intervertebral allograft spacer or implant 1510 according to the present invention is shown. Implant 1510 conforms in size and shape with a portion of end plates of the vertebrae between which implant 1510 is to be implanted. Because implant 1510 is an allograft, implant 1510 promotes the formation of new bone to fuse the two vertebral bodies together. Although implant 1510 will probably be predominantly used in the lumbar region of the spine, implant 1510 can be configured for implantation in any region of the spine. Implant 1510 has a plurality of teeth 1512 on superior and inferior surfaces 1514, 1516 which provide a mechanical interlock between implant 1510 and the end plates. Teeth 1512 provide the mechanical interlock by penetrating the end plates. The initial mechanical stability afforded by teeth 1512 minimizes the risk of post-operative expulsion of implant 1510. Teeth 1512 can be pyramid-shaped (FIG. 29A). Preferably, the angle formed from the tip to the base is approximately 60°. Alternatively, teeth 1512 have a saw tooth shape with the saw tooth running in the anterior-posterior direction (FIG. 29B).

Figure 21:
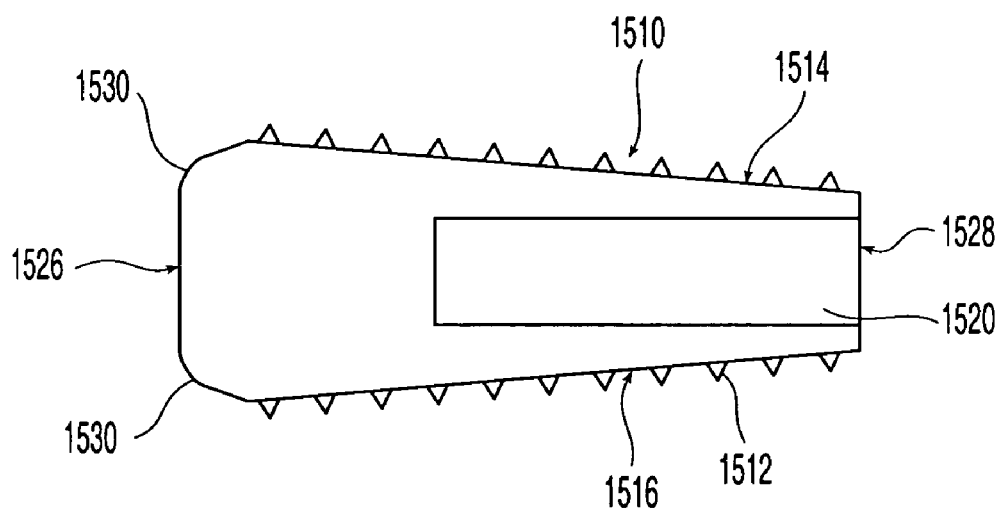
FIG. 21 is a side view of the implant of FIG. 20.
Figure 22:
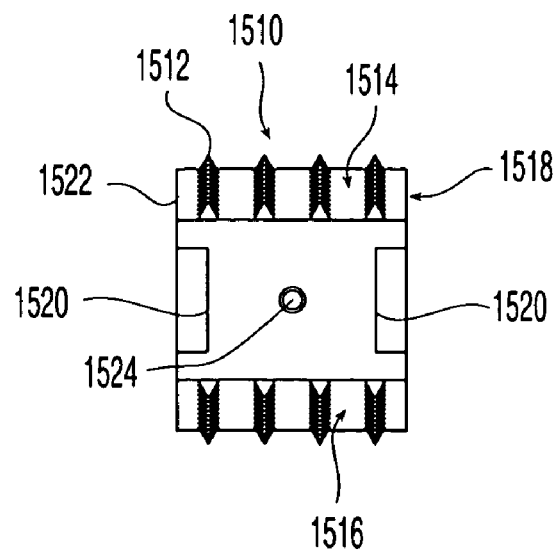
FIG. 22 is a back view of the implant of FIG. 20.
Figure 24:
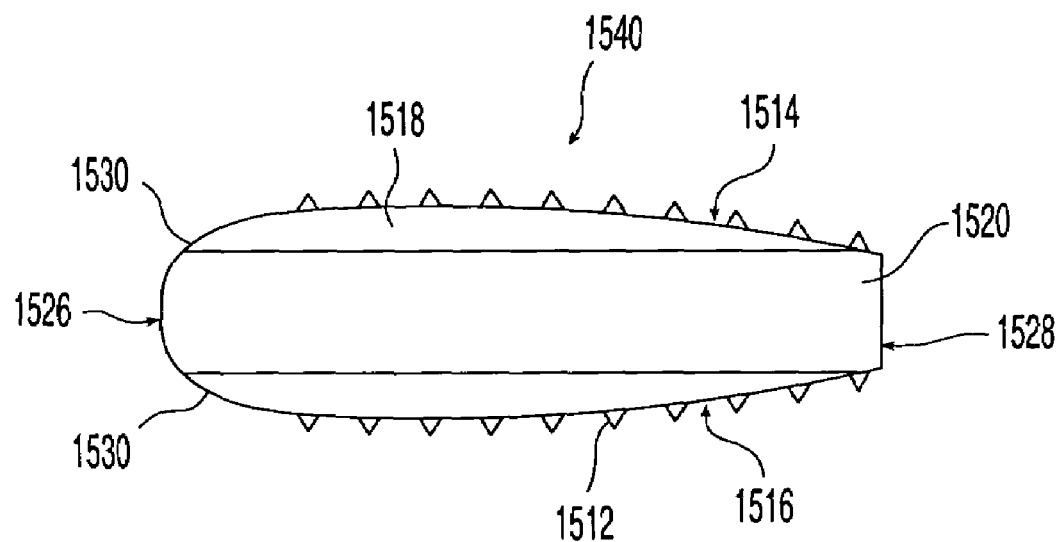
FIG. 24 is a side view of the implant of FIG. 23.

As shown in FIG. 21 and FIG. 22, a first lateral side 1518 has a channel 1520 and a second lateral side 1522 also has a channel 1520. Channels 1520 are sized to receive a surgical instrument such as an inserter for implantation of implant 1510. If the inserter has a threaded arm, implant 1510 can be provided with a threaded hole 1524. In FIG. 21, channel 1520 is shown extended only partially along first lateral side 1518. Channel 1520 can extend along the entire length of first lateral side 1518 as shown in the embodiment of FIG. 24. In FIG. 22, channels 1520 are shown on both first and second lateral sides 1518, 1522. It should be noted that implant 1510 can also have no channels or channels on one lateral side only as shown in the embodiment of FIG. 28.

The dimensions of implant 1510 can be varied to accommodate a patient's anatomy. Typically, implant 1510 would have a width between 6–15 mm (in the medial-lateral direction), a length between 15–30 mm (in the anterior-posterior direction), and a eight between 4–30 mm (maximum height in the superior-inferior direction). The size of implant 1510 allows implant 1510 to be implanted using conventional open surgical procedures or minimally invasive procedures, such as laparoscopic surgery. Additionally, because the width is kept to a restricted size range and does not necessarily increase with implant height, taller implants can be used without requiring wider implants. Thus, facet removal and retraction of nerve roots can remain minimal.

In order to restore the natural curvature of the spine after the affected disc has been removed, implant 1510 has a wedge-shaped profile. As shown in FIG. 21, this wedge shape results from a gradual decrease in height from an anterior side 1526 to a posterior side 1528. In anatomical terms, the natural curvature of the lumbar spine is referred to as lordosis. When implant 1510 is to be used in the lumbar region, the angle formed by the wedge should be approximately between 4.2° and 15° so that the wedge shape is a lordotic shape which mimics the anatomy of the lumbar spine.

In order to facilitate insertion of implant 1510, anterior side 1526 transitions to superior and inferior surfaces 1514, 1516 with rounded edges 1530. Rounded edges 1530 enable implant 1510 to slide between the end plates while minimizing the necessary distraction of the end plates.

Although implant 1510 is typically a solid piece of allogenic bone, implant 1510 can be provided with a hollow interior to form an interior space. This interior space can be filled with bone chips or any other osteoconductive material to further promote the formation of new bone.

Figure 23:
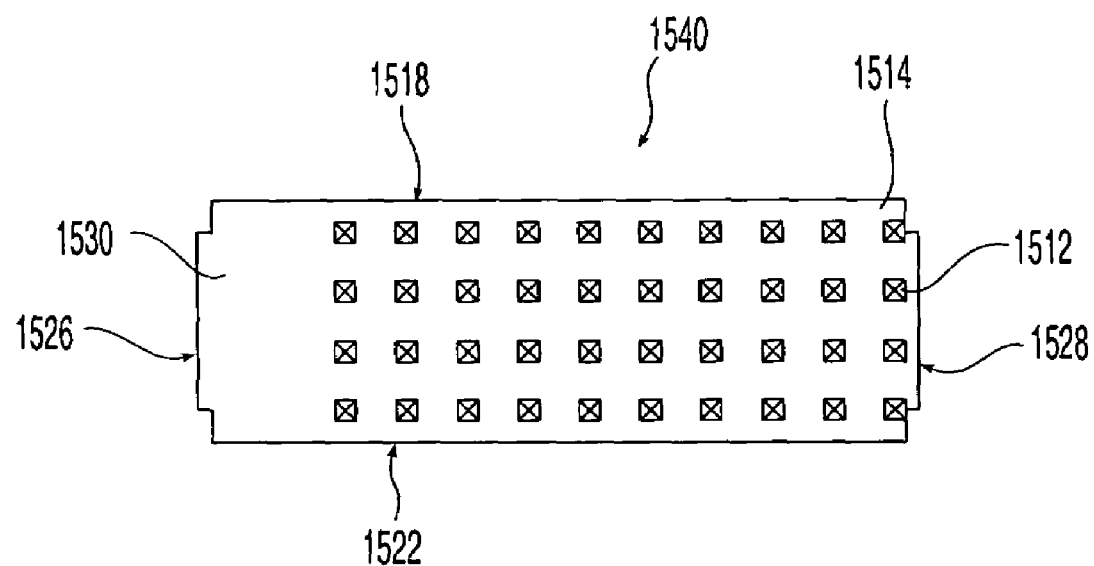
FIG. 23 is a top view of a yet another embodiment of an implant.

FIG. 23 shows a top view of another embodiment of an implant 1540 according to the present invention. In general, most of the structure of implant 1540 is like or comparable to the structure of implant 1510. Accordingly, discussion of the like components is not believed necessary. The superior and inferior surfaces 1514, 1516 of implant 1510 are flat planar surfaces. As seen best in FIG. 24, superior and inferior surfaces 1514, 1516 of implant 1540 are curved surfaces which still retain the wedge-shaped profile. The curved surfaces of superior and inferior surfaces 1514, 1516 of implant 1540 are a mirror-image of the topography of the vertebral end plates. Thus, the curved surfaces conform to the contours of the end plates.

Figure 25:
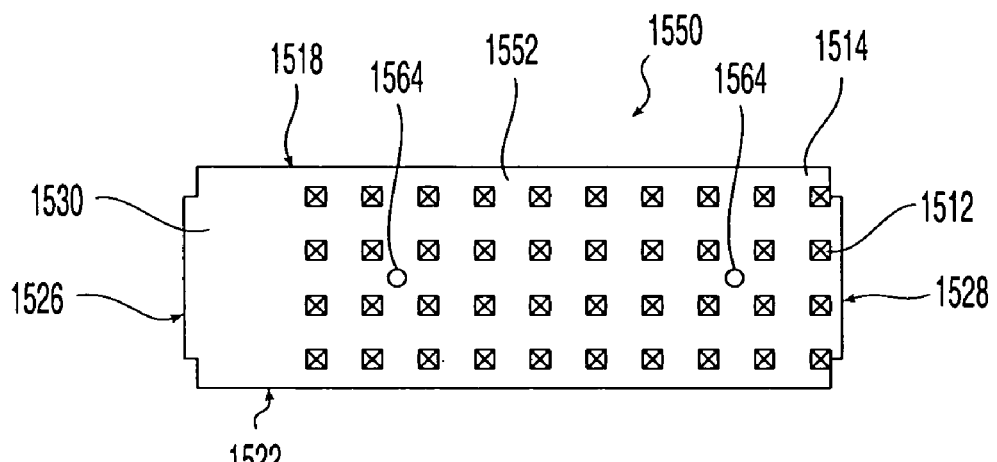
FIG. 25 is a top view of another embodiment of an implant.
Figure 26:
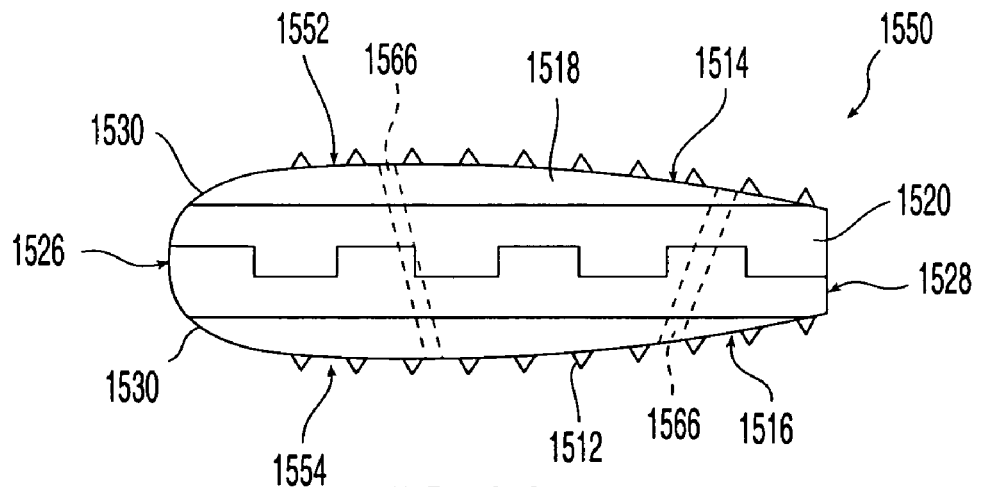
FIG. 26 is a side view of the implant of FIG. 25.
Figures 27A, 27B:
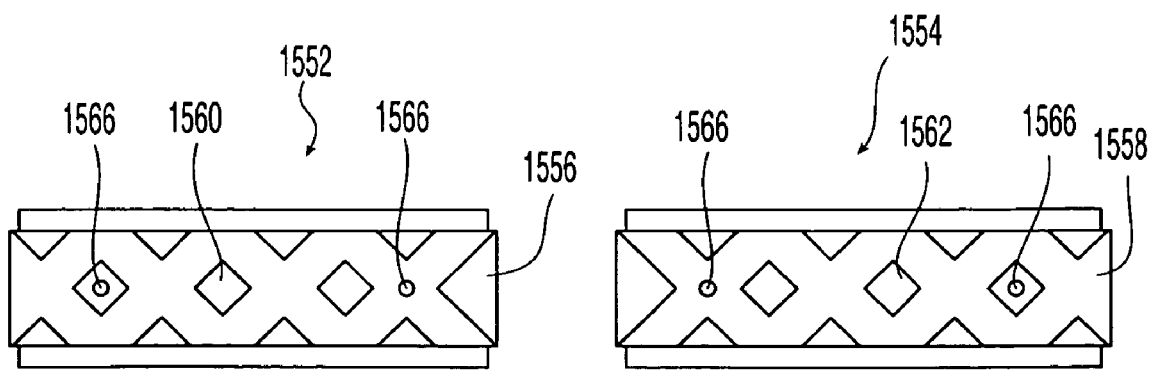
FIG. 27A is a top view of a top connecting surface of a top portion of the implant of FIG. 25.
FIG. 27B is a top view of a bottom connecting surface of a bottom portion of he implant of FIG. 25.

FIG. 25 shows a top view of an additional embodiment of an implant 1550 according to the present invention. In general, most of the structure of implant 1550 is like or comparable to the structure of implants 1510, 1540. Accordingly, discussion of the like components is not believed necessary. As best seen in FIG. 26, implant 1550 comprises a top portion 1552 joined to a bottom portion 1554. As it may be difficult to obtain a single section of allogenic bone from which implant 1550 is to be made, fabricating implant 1550 in two pieces, i.e. top and bottom portions 1552, 1554, allows smaller sections of allogenic bone to be used. A top connecting surface 1556 and a bottom connecting surface 1558 define the interface between top and bottom portions 1552, 1554. As shown in FIGS. 27A and 27B, top and bottom surfaces 1556, 1558 have ridges 1560 that mate with grooves 1562 to interlock top and bottom portions 1552, 1554. Preferably, ridges 1560 and grooves 1562 are formed by milling top and bottom surfaces 1556, 1558 in a first direction and then milling a second time with top and bottom surfaces 1556, 1558 oriented 90° with respect to the first direction.

A pin 1564 passing through aligned holes 1566 in top and bottom portions 1552, 1554 serves to retain top and bottom portions 1552, 1554 together. Although pin 1564 can be made of any biocompatible material, pin 1564 is preferably made of allogenic bone. The number and orientation of pins 1564 can be varied.

Figure 30:
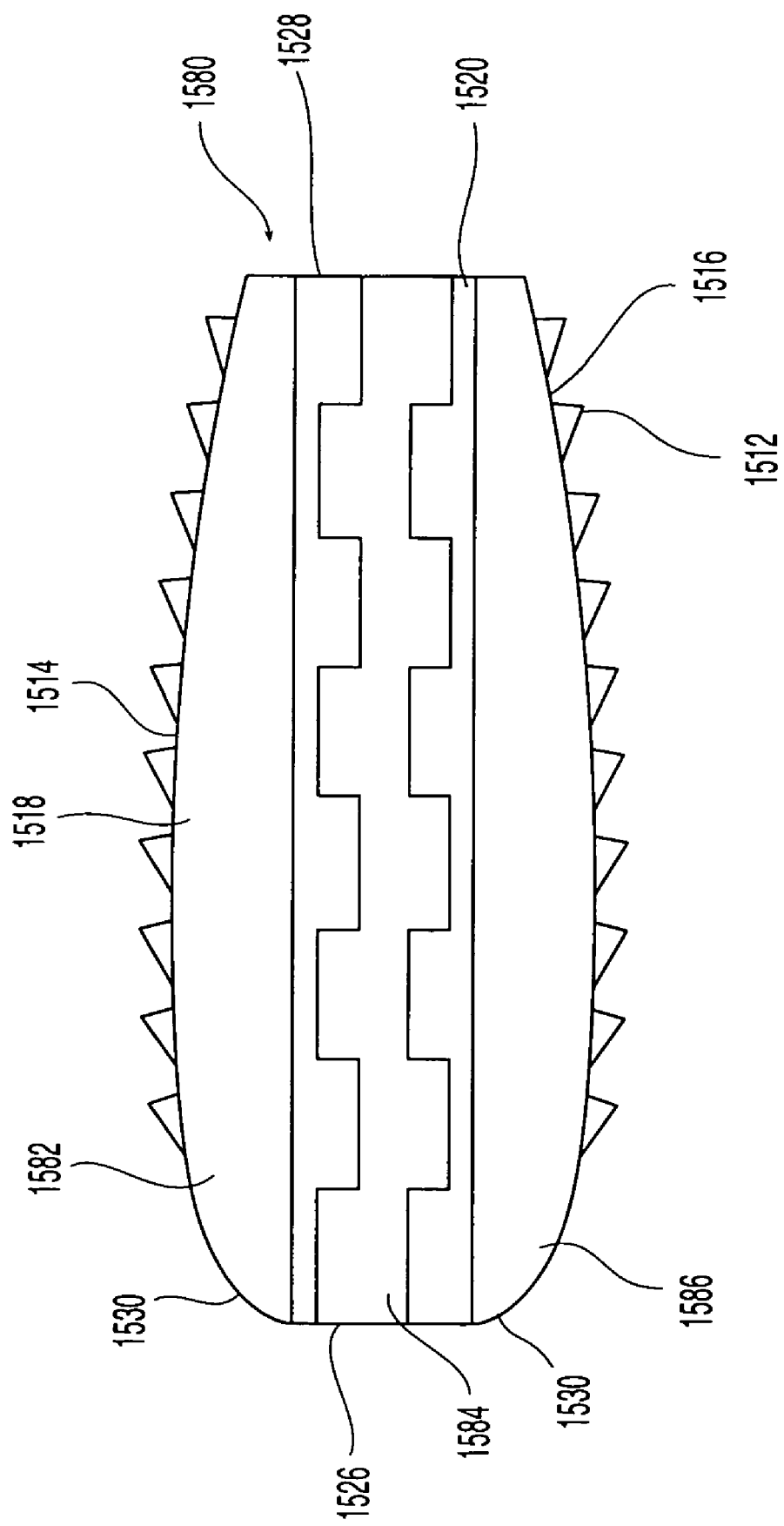
FIG. 30 is a side view of an embodiment of the implant similar to the embodiment of FIGS. 25–27.

FIG. 30 shows an embodiment of an implant 1580 which, like implant 1550, is made in multiple pieces. In general, most of the structure of implant 1580 is like or comparable to the structure of implants 1510, 1540, 1550. Accordingly, discussion of the like components is not believed necessary. Implant 1580 has a top portion 1582, a middle portion 1584, and a bottom portion 1586. As was the case for implant 1580, the surfaces between the portions are mating surfaces with interlocking surface features, such as ridges and grooves. One or more pins preferably hold top, middle, and bottom portions 1582, 1584, 1586 together.

FIG. 28 shows a perspective view of another embodiment of a first implant 1570 according to the present invention. A second implant 1570', which is substantially similar to first implant 1570, is also shown. In general, most of the structure of first and second implants 1570, 1570' is like or comparable to the structure of implants 1510, 1540, 1550. Accordingly, discussion of the like components is not believed necessary. First lateral sides 1518 of first and second implants 1570, 1570' are scalloped to have a C-shape. When first and second implants 1570, 1570' are placed side by side with the first lateral sides 1518 facing each other, a cylindrical space 1572 is formed. When first and second implants 1570, 1570' are implanted together, cylindrical space 1572 can be filled with osteoconductive material to help promote the formation of new bone. First and second implants 1570, 1570' can be provided with locking pins 1574 which engage apertures 1576 to maintain the spatial relationship between first and second implants 1570, 1570'.

Figure 32:
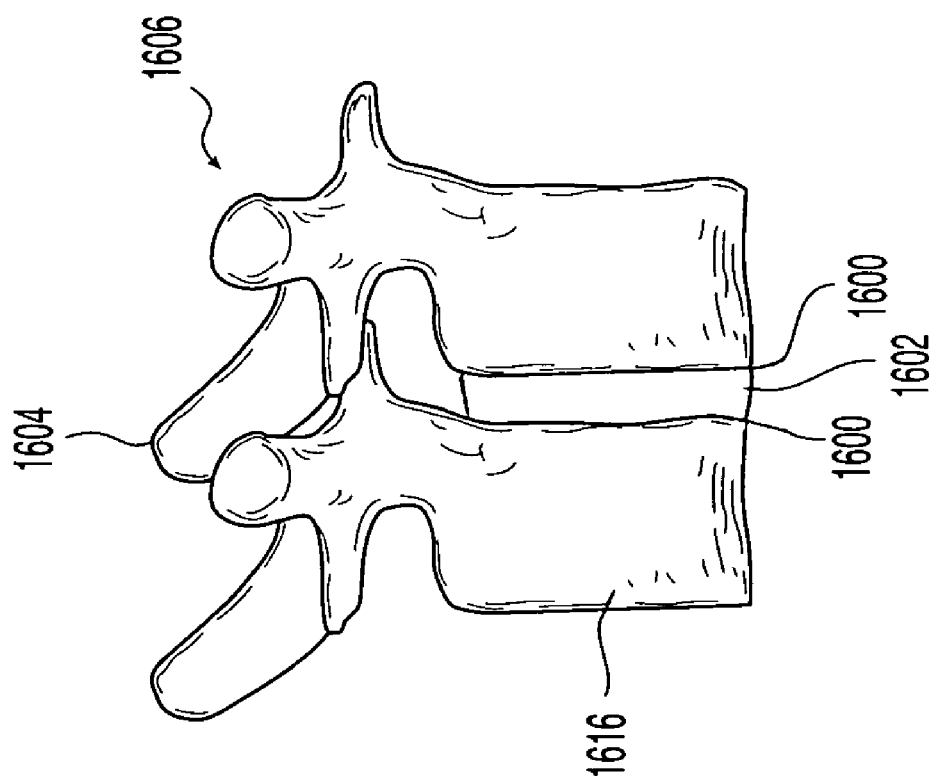
FIG. 32 is a side view of sequentially aligned vertebral bones, such as are found in the cervical, thoracic, or lumbar spine.
Figure 31:
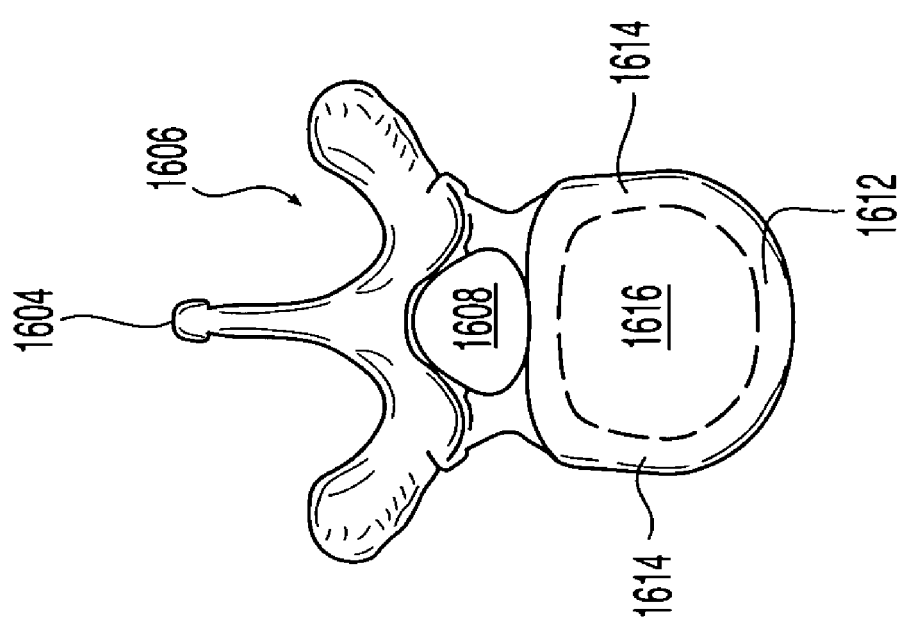
FIG. 31 is a top view of a vertebral bone characteristic of those of the cervical, thoracic, and lumbar spine.
Figure 33:
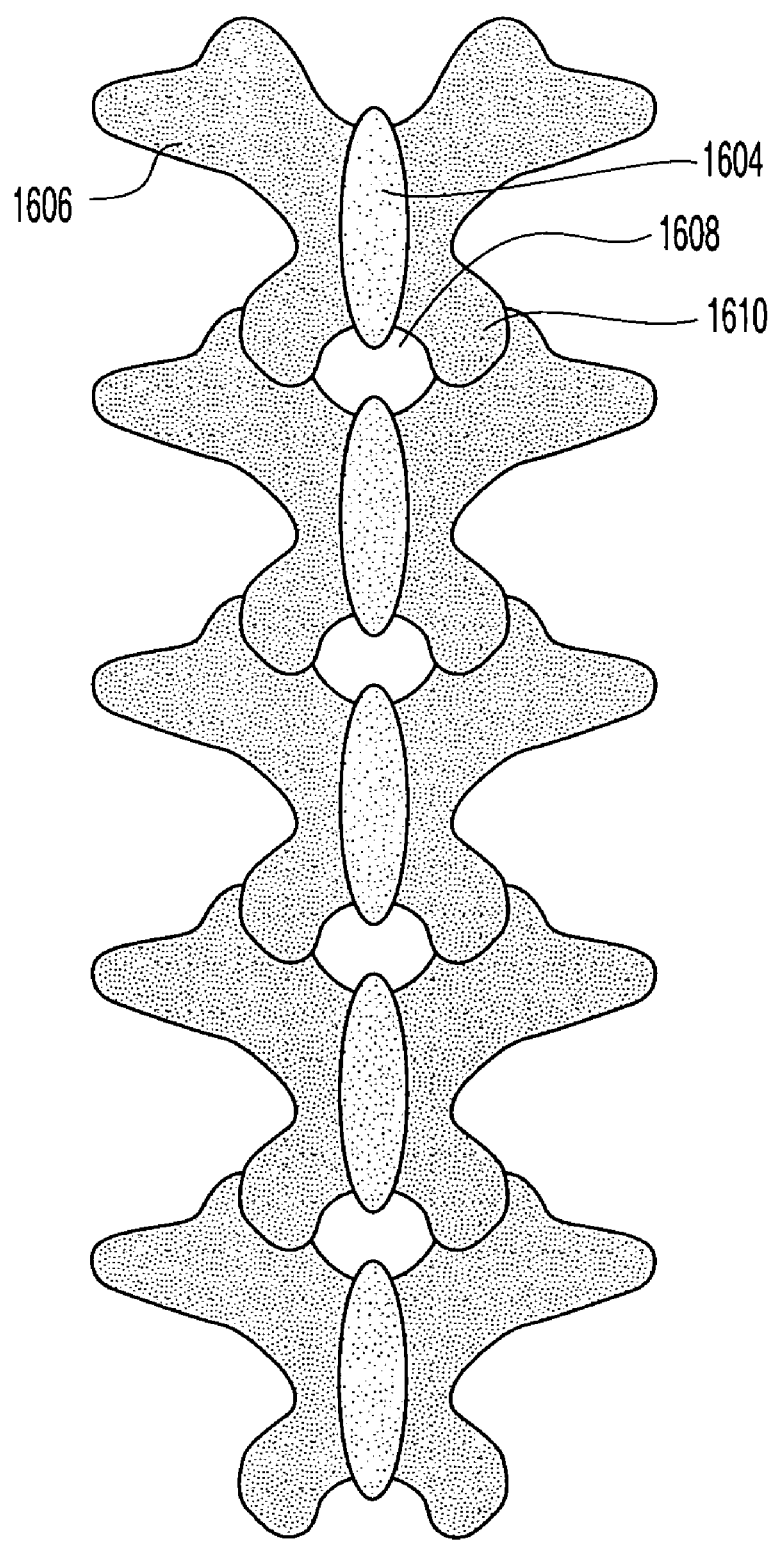
FIG. 33 is a posterior view of a sequence of vertebrae.

The use of the implant according to the present invention will now be described with reference to FIGS. 31–33 and using posterior lumbar interbody fusion as an example. As the implant according to the present invention conforms in size and shape to a portion of end plates 1600, preoperative planning is recommended for proper sizing. determine the appropriate implant height by measuring adjacent intervertebral discs 1602 on a lateral radiograph. The implant must be seated firmly with a tight fit between end plates 1600 when the segment is fully distracted. The tallest possible implant should be used to maximize segmental stability. Due to variability in degrees of magnification from radiographs, the measurements are only an estimate.

With the patient in a prone position on a lumbar frame, radiographic equipment can assist in confirming the precise intraoperative position of the implant. The surgeon incises and dissects the skin from the midline laterally and locates spinous process 1604, lamina 1606, dura 1608, and nerve roots of the appropriate level(s). As much as facets 1610 as possible should be preserved to provide stability to the intervertebral segment. The surgeon performs a laminotomy to the medial aspect of facet 1610 and reflects dura 1608 to expose an approximately 13 mm window to the disc space. Disc 1602 is removed through the window until only anterior 1612 and lateral 1614 annulus remain. The superficial layers of the entire cartilaginous end plates 1600 are also removed to expose bleeding bone. Excessive removal of the subchondral bone may weaken the anterior column. Furthermore, if the entire end plate is removed, this may result in subsidence and a loss of segmental stability.

Distraction can be done with either a surgical distractor or a trial spacer implant. In the first method, the distractor blades are placed into the disc space lateral to dura 1608. The curve on the neck of the distractor should be oriented toward the midline. The distractor blades should be completely inserted into the disc space so that the ridges at the end of the blades rest on vertebral body 1616. Fluoroscopy can assist in confirming that the distractor blades are parallel to end plates 1600. Correct placement will angle the handles of the distractor cranially, particularly at L5-S1. The handle of the distractor is squeezed to distract the innerspace. The distraction is secured by tightening the speed nut on the handle.

Using the preoperatively determined size, a trial spacer is inserted in the contralateral disc space with gentle impaction. Fluoroscopy and tactile judgement can assist in confirming the fit of the trial spacer until a secure fit is achieved. Using either the slots or threader hole on the implant, the selected implant is inserted in the contralateral disc space. Alternatively, the channels on the implant allow distraction and insertion to occur on the same side. Regardless of the side the implant is inserted in, autogenous cancellous bone or a bone substitute should be placed in the anterior and medial aspect of the vertebral disc space prior to placement of the second implant. The distractor is removed and a second implant of the same height as the first implant is inserted into the space, using gentle impaction as before. Preferably, the implants are recessed 2–4 mm beyond the posterior rim of the vertebral body.

Figure 34:
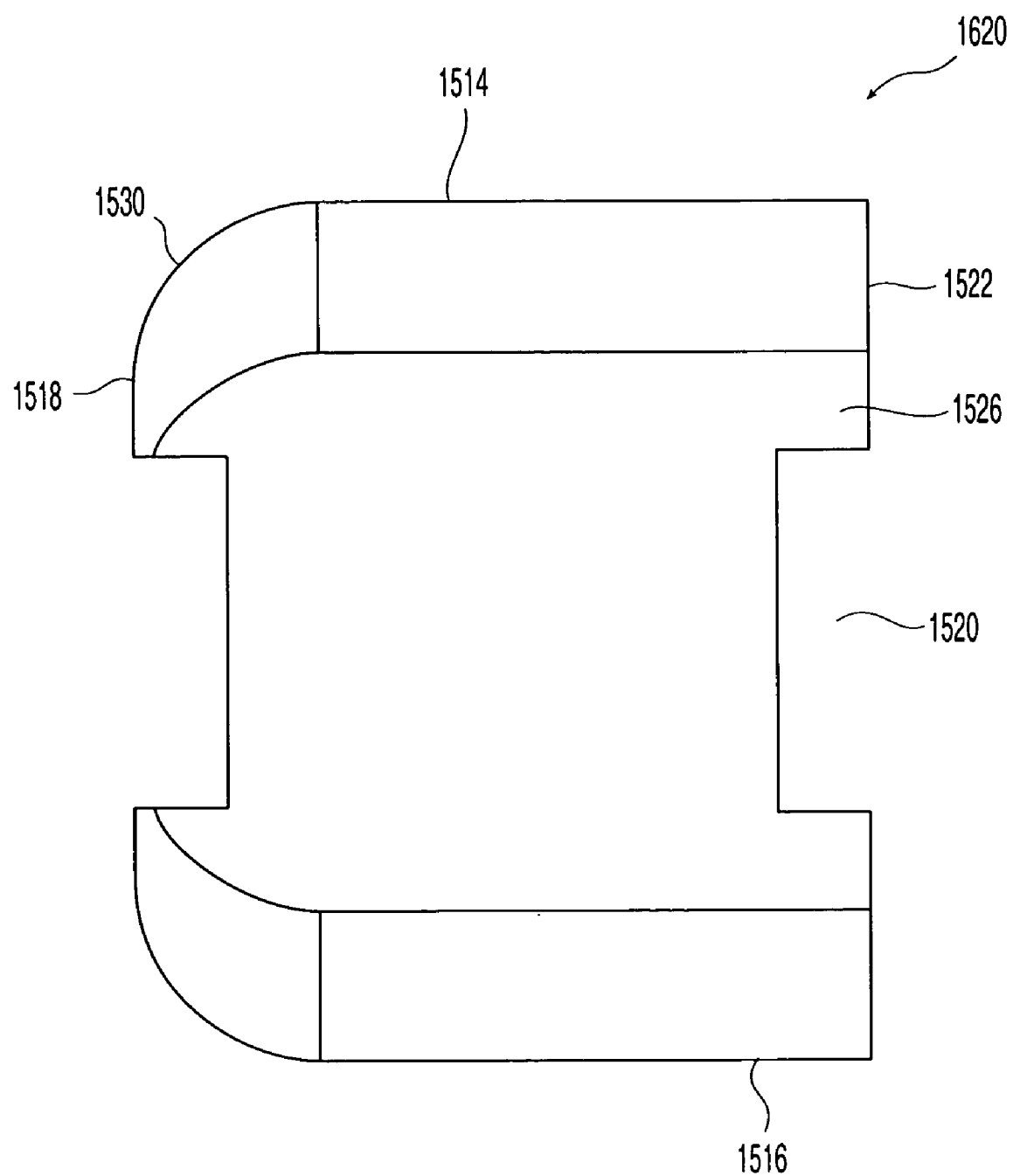
FIG. 34 is an end view of another embodiment of the implant.

As previously noted, the implant according to the present invention can be inserted using minimally invasive procedures. In some of these procedures, only one side of the spinal cord needs to be approached. This minimizes muscle stripping, scar tissue in the canal, and nerve root retraction and handling. In clinical situations in which bilateral implant placement is required, proper implantation on the side opposite the incision can be difficult. FIG. 34 shows a beveled spacer 1620 that facilitates placement on the side contralateral to the incision. In general and unless otherwise described, most of the structure of beveled spacer 1620 is like or comparable to the structure of implants 1510, 1540, 1550, and 1580. Accordingly, discussion of the like components is not believed necessary. First lateral side 1518 transitions to superior and inferior surfaces 1514, 1516 with rounded edges 1530. First lateral side 1518 also transitions to anterior and posterior sides 1526, 1528 with rounded edges 1530. Additionally, spacer 1620 has no teeth. The lack of teeth and rounded edges 1530 enable spacer 1620 to slide between the end plate and across the evacuated disc space (from one lateral annulus to the other) to the contralateral side. As first lateral side 1518 is the side that must promote movement of spacer 1620, the use of rounded edges 1530 on second lateral side 1522 is optionally. Once spacer 1620 has been placed on the side contralateral to the single incision using a surgical instrument to push spacer 1620, bone graft or other osteoconductive material is packed in the disc space. Finally, an implant (any of implant 1510, 1540, 1550, 1570, or 1570' can be used) is implanted in the side proximal to the incision.

While various descriptions of the present invention are described above, it should be understood that the various features can be used singly or in any combination thereof. The various types of joints and connections can be used on bone implants or bone stock of different size or configuration, such that the invention is not to be limited to only the specifically preferred embodiments depicted in the drawings.

Further, it should be understood that variations and modifications within the spirit and scope of the invention may occur to those skilled in the art to which the invention pertains. For example, multiple, differently shaped and sized bone portions can be constructed for interfitting or interconnection to form a multiple part bone implant that serves the desired purpose. Accordingly, all expedient modifications readily attainable by one versed in the art from the disclosure set forth herein are within the scope and spirit of the present invention and are to be included as further embodiments. The scope of the present invention is accordingly defined as set forth in the appended claims.

What is claimed is:

1. A bone fusion implant for repair or replacement of bone comprising a hollow body with a substantially enclosed hollow region formed by at least two bone fragments which are configured and dimensioned for mutual engagement and which are coupled together;
    wherein the at least two bone fragments are concentric hollow cylinders.

2. The implant of claim 1, further comprising a core formed of at least one of bone material and bone inducing substances, the core being disposed in the hollow body.

3. The implant of claim 2, wherein the core is formed of cancellous bone with a fluid concentrated therein.

4. The implant of claim 3, wherein the cancellous bone is subjected to mechanical pressure to concentrate the fluid.

5. The implant of claim 3, wherein the fluid is concentrated by soaking.

6. The implant of claim 4, wherein the mechanical pressure is applied by aspiration.

7. The implant of claim 1, wherein the hollow body comprises bone tissue selected from the group consisting of autograft, allograft, xenograft bone tissue, and combinations thereof.

8. The implant of claim 7, wherein the bone tissue of at least one of the bone fragments is partially demineralized or demineralized.

9. The implant of claim 1, wherein at least one of the bone fragments is at least partially dehydrated to mate against another bone fragment.

10. The implant of claim 1, further comprising an outer surface with a contour conforming in shape with the end plates of vertebrae.

11. A bone fusion implant for repair or replacement of bone comprising a hollow body formed from at least two bone fragments which are configured and dimensioned for mutual engagement and which are coupled together, wherein the hollow body further comprises a completely enclosed hollow region.

12. The implant of claim 11, wherein the at least two bone fragments comprise a first bone fragment with a first coupling portion and a second bone fragment with a second coupling portion, and wherein the first and second bone fragments are joined together by interfitting the first and second coupling portions.

13. The implant of claim 11, further comprising at least one of bone material and bone-growth inducing substance disposed in the hollow region.

14. The implant of claim 11, further comprising cancellous bone with a fluid concentrated therein, wherein the cancellous bone is disposed in the hollow region.

15. The implant of claim 11, wherein the bone tissue of at least one bone fragment is partially demineralized or demineralized.

16. The implant of claim 11, wherein at least one of the bone fragments is at least partially dehydrated to mate with another bone fragment.

17. The implant of claim 11, further comprising an outer surface with a contour conforming in shape with the end plates of vertebrae.

* * * * *